(12) United States Patent
Galon et al.

(10) Patent No.: US 12,291,752 B2
(45) Date of Patent: *May 6, 2025

(54) METHODS FOR PREDICTING THE SURVIVAL TIME AND TREATMENT RESPONSIVENESS OF A PATIENT SUFFERING FROM A SOLID CANCER WITH A SIGNATURE OF AT LEAST 7 GENES

(71) Applicants: INSERM (INSTITUT NATIONAL DE LA SANTE ET DE LA RECHERCHE MEDICALE), Paris (FR); ASSISTANCE PUBLIQUE-HOPITAUX DE PARIS (APHP), Paris (FR); UNIVERSITÉ PARIS CITÉ, Paris (FR)

(72) Inventors: Jerome Galon, Paris (FR); Franck Pages, Paris (FR); Bernard Mlecnik, Paris (FR); Gabriela Bindea, Paris (FR)

(73) Assignees: INSERM (INSTITUT NATIONAL DE LA SANTÉ ET DE LA RECHERCHE MÉDICALE), Paris (FR); UNIVERSITE DE PARIS DESCARTES, Paris (FR); ASSISTANCE PUBLIQUE-HÔPITAUX DE PARIS (APHP), Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/562,111

(22) Filed: Dec. 27, 2021

(65) Prior Publication Data
US 2022/0259665 A1 Aug. 18, 2022

Related U.S. Application Data

(63) Continuation of application No. 14/413,856, filed as application No. PCT/EP2013/064808 on Jul. 12, 2013, now Pat. No. 11,242,564.

(30) Foreign Application Priority Data

Jul. 12, 2012 (EP) ..................................... 12305836

(51) Int. Cl.
*C12Q 1/6886* (2018.01)
(52) U.S. Cl.
CPC ..... *C12Q 1/6886* (2013.01); *C12Q 2537/143* (2013.01); *C12Q 2600/112* (2013.01); *C12Q 2600/118* (2013.01); *C12Q 2600/158* (2013.01); *C12Q 2600/16* (2013.01)

(58) Field of Classification Search
CPC ............ C12Q 1/6886; C12Q 2600/112; C12Q 2600/118; C12Q 2600/158; C12Q 2600/16
See application file for complete search history.

(56) References Cited

U.S. PATENT DOCUMENTS

| 5,595,756 A * | 1/1997 | Bally | A61K 9/1272 |
| | | | 264/4.1 |
| 2009/0215053 A1* | 8/2009 | Galon | G01N 33/57492 |
| | | | 435/6.16 |

FOREIGN PATENT DOCUMENTS

WO WO-2011094483 A2 * 8/2011 .............. A61P 35/00

OTHER PUBLICATIONS

Tockman et al. Considerations in bringing a cancer biomarker to clinical application. Cancer Res., 1992, 52:2711 s-2718s (Year: 1992).*
Ahmadzada et al. An Update on Predictive Biomarkers for Treatment Selection in Non-Small Cell Lung Cancer. J Clin Med. Jun. 15, 2018;7(6):153 (Year: 2018).*
McKean et al. Biomarkers in Precision Cancer Immunotherapy: Promise and Challenges. Am Soc Clin Oncol Educ Book. May 2020;40:e275-e291 (Year: 2020).*
Christiansen et al. Biological impediments to monoclonal antibody-based cancer immunotherapy. Mol Cancer Ther, 2004, 3:1493-1501 (Year: 2004).*
Topp et al. Antibody transport in cultured tumor cell layers. Journal of Controlled Release, 1998, 53:15-23 (Year: 1998).*
Heppner et al. Tumor heterogeneity: biological implications and therapeutic consequences. Cancer Metastasis Review 2:5-23; 1983 (Year: 1983).*

(Continued)

*Primary Examiner* — Vanessa L. Ford
*Assistant Examiner* — Sandra Carter
(74) *Attorney, Agent, or Firm* — WCF IP

(57) ABSTRACT

The present invention relates to a method for predicting the survival time of a patient suffering from a solid cancer comprising i) determining in a tumor sample obtained from the patient the gene expression level of at least 7 genes selected from the group consisting of CCR2, CD3D, CD3E, CD3G, CD8A, CXCL10, CXCL11, GZMA, GZMB, GZMK, GZMM, IL15, IRF1, PRF1, STAT1, CD69, ICOS, CXCR3, STAT4, CCL2, and TBX21, ii) comparing every expression level determined at step i) with their predetermined reference value and iii) providing a good prognosis when all expression levels determined at step i) are higher than their predetermined reference values, or providing a bad prognosis when all expression levels determined at step i) are lower than their predetermined reference values or providing an intermediate prognosis when at least one expression level determined value is higher than its predetermined value. The method is also particularly suitable for predicting the responsiveness of the patient to a treatment.

2 Claims, 11 Drawing Sheets

(56) References Cited

OTHER PUBLICATIONS

Sporn et al. Chemoprevention of Cancer, Carcinogenesis, vol. 21 (2000), 525-530 (Year: 2000).*
Auerbach et al. Angiogenesis assays: problems and pitfalls. Cancer and Metastasis Reviews, 2000, 19: 167-172 (Year: 2000).*
Gura T. Systems for identifying new frugs are often faulty. Science, 1997, 278(5340): 1041-1042 (Year: 1997).*
Jain RK. Barriers to drug delivery in solid tumors. Scientific American, Jul. 1994,58-65 (Year: 1994).*
Hait. Anticancer drug development: the grand challenges. Nature Reviews/Drug Discovery, 2010, 9, pp. 253-254 (Year: 2010).*
Gravanis et al. The changing world of cancer drug development: the regulatory bodies' perspective. Chin Clin Oncol, 2014, 3, pp. 1-5 (Year: 2014).*
Beans. Targetingmetastasis to halt cancer's spread. PNAS 2018; 115(50): 12539-12543 (Year: 2018).*

* cited by examiner

METHODS FOR PREDICTING THE SURVIVAL TIME AND TREATMENT RESPONSIVENESS OF A PATIENT SUFFERING FROM A SOLID CANCER WITH A SIGNATURE OF AT LEAST 7 GENES

FIELD OF THE INVENTION

The present invention relates to methods and kits for predicting the survival time and responsiveness of a patient suffering from a solid cancer.

BACKGROUND OF THE INVENTION

Cancer remains a serious public health problem in developed countries. Accordingly, to be most effective, cancer treatment requires not only early detection and treatment or removal of the malignancy, but a reliable assessment of the severity of the malignancy and a prediction of the likelihood of cancer recurrence. The stage of a cancer indicates how far a cancer has spread. Staging is important because treatment is often decided according to the stage of a cancer. To date, cancers are generally classified according to the UICC-TNM system. The TNM (for "Tumor-Node-Metastasis") classification system uses the size of the tumor, the presence or absence of tumor in regional lymph nodes, and the presence or absence of distant metastases, to assign a stage to the tumor. The TNM system developed from the observation that patients with small tumours have better prognosis than those with tumours of greater size at the primary site. In general, patients with tumours confined to the primary site have better prognosis than those with regional lymph node involvement, which in turn is better than for those with distant spread of disease to other organs. Accordingly, cancer can be generally divided into four stages. Stage I is very localized cancer with no cancer in the lymph nodes. Stage II cancer has spread deeper into the primary organ, typically T3, T4 tumors. Stage III cancer has spread to the lymph nodes. Stage IV cancer has spread to another part of the body. The assigned stage is used as a basis for selection of appropriate therapy and for prognostic purposes. For example chemotherapy is always recommended for patients with stage IV cancers. On the contrary, there are no relevant guidelines for prescribing chemotherapy for patient with a UICC-TNM stage II or III cancer. Accordingly there is a need for reliable diagnostic tools to guide treatment decisions is all the more as an essential step for the multitude of available new therapies is the efficient selection of patients for adequate cancer therapy.

The above TNM classifications, although they are to be useful, are imperfect and do not allow a reliable prognosis of the outcome of the cancers. Recently, Galon et al. suggested that analysing the expression of genes related to the adaptive immune response within the tumour may be suitable for predicting the outcome of a cancer in a patient (WO2007045996). Thus they provides list of genes and combination thereof that may be useful for the prognosis of patients for progression of cancer. However the methods depicted in said document fail to point out particular combinations of genes that provide a better performance than the TNM classification does for predicting the survival time of patient with a cancer and for predicting the treatment response of the patient.

SUMMARY OF THE INVENTION

The present invention relates to methods and kits for predicting the survival time and responsiveness of a patient suffering from a solid cancer.

DETAILED DESCRIPTION OF THE INVENTION

International patent application WO2007045996 pertains to a general selection of the most important genes (~300) describing the tumour micro-environment that was done without considering combinations among them. To restrict the number of signatures, only 7 to 21 genes were used that remained highly logrank significant after 100x cross-validation on a cohort of patients. The genes are selected from the group consisting of CCR2, CD3D, CD3E, CD3G, CD8A, CXCL10, CXCL11, GZMA, GZMB, GZMK, GZMM, IL15, IRF1, PRF1, STAT1, CD69, ICOS, CXCR3, STAT4, CCL2, and TBX2. For example the possible number of non redundant signatures of around 21 out of 300 genes described in international patent application WO2007045996 exceeds 1.0E+37.The inventors demonstrate that the identified a signature of 21 genes provides a greater sensitivity and selectivity than the UICC-TNM classification does. They validate the signatures on different cancers. Furthermore the inventors demonstrated that the same signature is suitable for predicting the responsiveness of the patient to a treatment.

Accordingly, the present invention relates to a method for predicting the survival time of a patient suffering from a solid cancer comprising i) determining in a tumor sample obtained from the patient the gene expression level of at least 7 genes selected from the group consisting of CCR2, CD3D, CD3E, CD3G, CD8A, CXCL10, CXCL11, GZMA, GZMB, GZMK, GZMM, IL15, IRF1, PRF1, STAT1, CD69, ICOS, CXCR3, STAT4, CCL2, and TBX21 ii) comparing every expression level determined at step i) with their predetermined reference value and iii)
- providing a good prognosis when all expression levels determined at step i) are higher than their predetermined reference values, or
- providing a bad prognosis when all expression levels determined at step i) are lower than their predetermined reference values or
- providing an intermediate prognosis when at least one expression level determined value is higher than its predetermined value.

The present invention also relates to a method for predicting the survival time of a patient suffering from a solid cancer comprising i) determining in a tumor sample obtained from the patient the gene expression level of CCR2, CD3D, CD3E, CD3G, CD8A, CXCL10, CXCL11, GZMA, GZMB, GZMK, GZMM, IL15, IRF1, PRF1, STAT1, CD69, ICOS, CXCR3, STAT4, CCL2, and TBX21 ii) comparing every expression level determined at step i) with their predetermined reference value and iii)
- providing a good prognosis when all expression levels determined at step i) are higher than their predetermined reference values, or
- providing a bad prognosis when all expression levels determined at step i) are lower than their predetermined reference values or
- providing an intermediate prognosis when at least one expression level determined value is higher than its predetermined value.

With respect to intermediate prognosis, every time that the expression level of a gene is higher than its predetermined reference value, the more favourable will be the prognosis of the patient.

The patient may suffer from any solid cancer. Typically, the cancer may be selected from the group consisting of bile duct cancer (e.g. periphilar cancer, distal bile duct cancer, intrahepatic bile duct cancer), bladder cancer, bone cancer (e.g. osteoblastoma, osteochrondroma, hemangioma, chondromyxoid fibroma, osteosarcoma, chondrosarcoma, fibrosarcoma, malignant fibrous histiocytoma, giant cell tumor of the bone, chordoma, lymphoma, multiple myeloma), brain and central nervous system cancer (e.g. meningioma, astocytoma, oligodendrogliomas, ependymoma, gliomas, medulloblastoma, ganglioglioma, Schwannoma, germinoma, craniopharyngioma), breast cancer (e.g. ductal carcinoma in situ, infiltrating ductal carcinoma, infiltrating, lobular carcinoma, lobular carcinoma in, situ, gynecomastia), Castleman disease (e.g. giant lymph node hyperplasia, angiofollicular lymph node hyperplasia), cervical cancer, colorectal cancer, endometrial cancer (e.g. endometrial adenocarcinoma, adenocanthoma, papillary serous adnocarcinroma, clear cell), esophagus cancer, gallbladder cancer (mucinous adenocarcinoma, small cell carcinoma), gastrointestinal carcinoid tumors (e.g. choriocarcinoma, chorioadenoma destruens), Hodgkin's disease, non-Hodgkin's lymphoma, Kaposi's sarcoma, kidney cancer (e.g. renal cell cancer), laryngeal and hypopharyngeal cancer, liver cancer (e.g. hemangioma, hepatic adenoma, focal nodular hyperplasia, hepatocellular carcinoma), lung cancer (e.g. small cell lung cancer, non-small cell lung cancer), mesothelioma, plasmacytoma, nasal cavity and paranasal sinus cancer (e.g. esthesioneuroblastoma, midline granuloma), nasopharyngeal cancer, neuroblastoma, oral cavity and oropharyngeal cancer, ovarian cancer, pancreatic cancer, penile cancer, pituitary cancer, prostate cancer, retinoblastoma, rhabdomyosarcoma (e.g. embryonal rhabdomyosarcoma, alveolar rhabdomyosarcoma, pleomorphic rhabdomyosarcoma), salivary gland cancer, skin cancer (e.g. melanoma, nonmelanoma skin cancer), stomach cancer, testicular cancer (e.g. seminoma, nonseminoma germ cell cancer), thymus cancer, thyroid cancer (e.g. follicular carcinoma, anaplastic carcinoma, poorly differentiated carcinoma, medullary thyroid carcinoma, thyroid lymphoma), vaginal cancer, vulvar cancer, and uterine cancer (e.g. uterine leiomyosarcoma). In a particular embodiment, the cancer is a colorectal cancer.

The term "tumor sample" means any tissue tumor sample derived from the patient. Said tissue sample is obtained for the purpose of the in vitro evaluation. The sample can be fresh, frozen, fixed (e.g., formalin fixed), or embedded (e.g., paraffin embedded). In a particular embodiment the tumor sample may result from the tumor resected from the patient. In another embodiment, the tumor sample may result from a biopsy performed in the primary tumour of the patient or perfomed in metastatic sample distant from the primary tumor of the patient. For example an endoscopical biopsy performed in the bowel of the patient affected by a colorectal cancer.

All the genes pertaining to the invention are known per se, and are listed in the below Tables A:

| Gene | Name | Gene ID |
|------|------|---------|
| CCR2 | chemokine (C-C motif) receptor 2 | 729230 |

-continued

| Gene | Name | Gene ID |
|------|------|---------|
| CD3D | CD3d molecule, delta (CD3-TCR complex) | 915 |
| CD3E | CD3e molecule, epsilon (CD3-TCR complex) | 916 |
| CD3G | CD3g molecule, gamma (CD3-TCR complex) | 917 |
| CD8A | CD8a molecule | 925 |
| CXCL10 | chemokine (C-X-C motif) ligand 10 | 3627 |
| CXCL11 | hemokine (C-X-C motif) ligand 11 | 6373 |
| GZMA | granzyme A (granzyme 1, cytotoxic T-lymphocyte-associated serine esterase 3) | 3001 |
| GZMB | granzyme B (granzyme 2, cytotoxic T-lymphocyte-associated serine esterase 1) | 3002 |
| GZMK | granzyme K (granzyme 3; tryptase II) | 3003 |
| GZMM | granzyme M (lymphocyte met-ase 1) | 3004 |
| IL15 | interleukin 15 | 3600 |
| IRF1 | interferon regulatory factor 1 | 3659 |
| PRF1 | perforM 1 (pore forming protein) | 5551 |
| STAT 1 | signal transducer and activator of transcription 1, 91 kDa | 6772 |
| CD69 | CD69 molecule | 969 |
| ICOS | inducible T-cell co-stimulator | 29851 |
| CXCR3 | chemokine (C-X-C motif) receptor 3 | 2833 |
| STAT4 | signal transducer and activator of transcription 4 | 6775 |
| CCL2 | chemokine (C-C motif) ligand 2 | 6347 |
| TBX21 | T-box 21 | 30009 |

CCR2, CD3D, CD3E, CD3G, CD8A, CXCL10, CXCL11, GZMA, GZMB, GZMK, GZMM, IL15, IRF1, PRF1, STAT1, CD69, ICOS, CXCR3, STAT4, CCL2, and TBX21

Thus the present invention may include:
determining the expression level of CCR2 ($EL_{CCR2}$) and comparing said level with the predetermined reference level for CCR2 ($ELR_{CCR2}$),
determining the expression level of CD3D ($EL_{CD3D}$) and comparing said level with the predetermined reference level for CD3D ($ELR_{CD3D}$),
determining the expression level of CD3E ($EL_{CD3E}$) and comparing said level with the predetermined reference level for CD3E ($ELR_{CD3E}$),
determining the expression level of CD3G ($EL_{CD3G}$) and comparing said level with the predetermined reference level for CD3G ($ELR_{CD3G}$),
determining the expression level of CD8A ($EL_{CD8A}$) and comparing said level with the predetermined reference level for CD8A ($ELR_{CD8A}$),
determining the expression level of CXCL10 ($EL_{CXCL}10$) and comparing said level with the predetermined reference level for CXCL10 ($ELR_{CXCL}10$),
determining the expression level of CXCL11 ($EL_{CXCL11}$) and comparing said level with the predetermined reference level for CXCL11 ($ELR_{CXCL11}$),
determining the expression level of GZMA ($EL_{GZMA}$) and comparing said level with the predetermined reference level for GZMA ($ELR_{GZMA}$),
determining the expression level of GZMB ($EL_{GZMB}$) and comparing said level with the predetermined reference level for GZMB ($ELR_{GZMB}$), determining the expression level of GZMK ($EL_{GZMK}$) and comparing said level with the predetermined reference level for GZMK ($ELR_{GZMK}$), determining the expression level of GZMM ($EL_{GZMM}$) and comparing said level with the predetermined reference level for GZMM ($ELR_{GZMM}$), determining the expression level of IL15 ($EL_{IL15}$) and comparing said level with the predetermined reference level for IL15 ($ELR_{IL15}$), determining the expression level of IRF1 ($EL_{IRF1}$) and comparing said level with the predetermined reference level for IRF1 ($ELR_{IRF1}$), determining the expression level of PRF1 ($EL_{PRF1}$) and comparing said level with the predetermined reference level for PRF1($ELR_{PRF1}$), determining the expression level of STAT1 ($EL_{STAT1}$) and comparing said level with the predetermined reference level for STAT1($ELR_{STAT1}$), determining the expression level of CD69 ($EL_{CD69}$) and comparing said level with the predetermined reference level for CD69 ($ELR_{CD69}$), determining the expression level of ICOS ($EL_{ICOS}$) and comparing said level with the predetermined reference level for ICOS ($ELR_{ICOS}$), determining the expression level of CXCR3 ($EL_{CXCR3}$) and comparing said level with the predetermined reference level for CXCR3 ($ELR_{CXCR3}$), determining the expression level of STAT4 ($EL_{STAT4}$) and comparing said level with the predetermined reference level for STAT4 ($ELR_{STAT4}$), determining the expression level of CCL2 ($EL_{CCL2}$) and comparing said level with the predetermined reference level for CCL2 ($ELR_{CCL2}$), determining the expression level of TBX21 ($EL_{TBX21}$) and comparing said level with the predetermined reference level for TBX21 ($ELR_{TBX21}$), The present invention also relates to a method for predicting the survival time of a patient suffering from a breast cancer comprising i) determining in a tumor sample obtained from the patient the gene expression level of CCR2, GZMB, GZMK, STAT1, ICOS, STAT4, and TBX21 ii) comparing every expression level determined at step i) with their predetermined reference value and providing a good prognosis when all expression levels determined at step i) are higher than their predetermined reference values, or providing a bad prognosis when all expression levels determined at step i) are lower than their predetermined reference values or providing an intermediate prognosis when at least one expression level determined value is higher than its predetermined value.

The present invention also relates to a method for predicting the survival time of a patient suffering from a breast cancer comprising i) determining in a tumor sample obtained from the patient the gene expression level of CCR2, CD3D, CD3E, CD3G, CD8A, CXCL10, CXCL11, GZMA, GZMB, GZMK, GZMM, IL15, IRF1, PRF 1, CD69, ICOS, CXCR3, and STAT4 ii) comparing every expression level determined at step i) with their predetermined reference value and iii)

providing a good prognosis when all expression levels determined at step i) are higher than their predetermined reference values, or providing a bad prognosis when all expression levels determined at step i) are lower than their predetermined reference values or providing an intermediate prognosis when at least one expression level determined value is higher than its predetermined value.

The present invention also relates to a method for predicting the survival time of a patient suffering from a cervical cancer comprising i) determining in a tumor sample obtained from the patient the gene expression level of CD3E, CD3G, CD8A, CXCL11, GZMA, GZMB, GZMK, GZMM, IL15, IRF1, CD69, ICOS, CXCR3, STAT4, CCL2, and TBX21 ii) comparing every expression level determined at step i) with their predetermined reference value and iii)

providing a good prognosis when all expression levels determined at step i) are higher than their predetermined reference values, or providing a bad prognosis when all expression levels determined at step i) are lower than their predetermined reference values or providing an intermediate prognosis when at least one expression The present invention also relates to a method for predicting the survival time of a patient suffering from a hepatocellular carcinoma comprising i) determining in a tumor sample obtained from the patient the gene expression level of CCR2, CD3D, CD3E, CD8A, CXCL10, GZMA, GZMM, IL15, IRF1, PRF1, STAT1, CD69, CXCR3, and STAT4 ii) comparing every expression level determined at step i) with their predetermined reference value and iii)

providing a good prognosis when all expression levels determined at step i) are higher than their predetermined reference values, or providing a bad prognosis when all expression levels determined at step i) are lower than their predetermined reference values or providing an intermediate prognosis when at least one expression The present invention also relates to a method for predicting the survival time of a patient suffering from a lung cancer comprising i) determining in a tumor sample obtained from the patient the gene expression level of CCR2, CD3D, CD3E, CD3G, CD8A, CXCL11, GZMA, GZMB, GZMK, GZMM, IL15, IRF1, PRF1, STAT1, CD69, STAT4, and CCL2, ii) comparing every expression level determined at step i) with their predetermined reference value and iii)

providing a good prognosis when all expression levels determined at step i) are higher than their predetermined reference values, or providing a bad prognosis when all expression levels determined at step i) are lower than their predetermined reference values or providing an intermediate prognosis when at least one expression The present invention also relates to a method for predicting the survival time of a patient suffering from a melanoma comprising i) determining in a tumor sample obtained from the patient the gene expression level of CCR2, CD3D, CD3E, CD3G, CD8A, CXCL10, GZMA, GZMB, GZMK, GZMM, IRF1, PRF1, CD69, ICOS, CXCR3 and TBX21 ii) comparing every expression level determined at step i) with their predetermined reference value and iii)

providing a good prognosis when all expression levels determined at step i) are higher than their predetermined reference values, or providing a bad prognosis when all expression levels determined at step i) are lower than their predetermined reference values or providing an intermediate prognosis when at least one expression The present invention also relates to a method for predicting the survival time of a patient suffering from an ovarian cancer comprising i) determining in a tumor sample obtained from the patient the gene expression level of CD3D, CD3E, CD3G, CD8A, CXCL10, CXCL11, GZMA, GZMB, GZMK, IRF1, PRF1, STAT1, ICOS, CXCR3, STAT4, CCL2, and TBX21 ii) comparing every expression level determined at step i) with their predetermined reference value and iii)

providing a good prognosis when all expression levels determined at step i) are higher than their predetermined reference values, or providing a bad prognosis when all expression levels determined at step i) are lower than their predetermined reference values or providing an intermediate prognosis when at least one expression The present invention also relates to a method for predicting the survival time of a patient suffering from an ovarian cancer comprising i) determining in a tumor sample obtained from the patient the gene expression level of CD3E, CD3G, CXCL10, CXCL11, GZMB, GZMK, IRF1, PRF1, STAT1, ICOS, CXCR3, CCL2, and TBX21 ii) comparing every expression level determined at step i) with their predetermined reference value and iii)

providing a good prognosis when all expression levels determined at step i) are higher than their predetermined reference values, or providing a bad prognosis when all expression levels determined at step i) are lower than their predetermined reference values or providing an intermediate prognosis when at least one expression The present invention also relates to a method for predicting the survival time of a patient suffering from a pancreatic cancer comprising i) determining in a tumor sample obtained from the patient the gene expression level of CD3G, CD8A, CXCL11, GZMA, GZMK, GZMM, IL15, IRF1, PRF1, STAT1, ICOS, CXCR3, STAT4, and TBX21 ii) comparing every expression level determined at step i) with their predetermined reference value and iii)

providing a good prognosis when all expression levels determined at step i) arc higher than their predetermined reference values, or providing a bad prognosis when all expression levels determined at step i) are lower than their predetermined reference values or providing an intermediate prognosis when at least one expression level determined value is higher than its predetermined value.

Measuring the expression level of a gene can be performed by a variety of techniques well known in the art.

Typically, the expression level of a gene may be determined by determining the quantity of mRNA. Methods for determining the quantity of mRNA arc well known in the art. For example the nucleic acid contained in the samples (e.g., cell or tissue prepared from the patient) is first extracted according to standard methods, for example using lytic enzymes or chemical solutions or extracted by nucleic-acid-binding resins following the manufacturer's instructions. The extracted mRNA is then detected by hybridization (e. g., Northern blot analysis, in situ hybridization) and/or amplification (e.g., RT-PCR).

Other methods of Amplification include ligase chain reaction (LCR), transcription-mediated amplification (TMA), strand displacement amplification (SDA) and nucleic acid sequence based amplification (NASBA).

Nucleic acids having at least 10 nucleotides and exhibiting sequence complementarity or homology to the mRNA of interest herein find utility as hybridization probes or amplification primers. It is understood that such nucleic acids need not be identical, but are typically at least about 80% identical to the homologous region of comparable size, more preferably 85% identical and even more preferably 90-95% identical. In certain embodiments, it will be advantageous to use nucleic acids in combination with appropriate means, such as a detectable label, for detecting hybridization.

Typically, the nucleic acid probes include one or more labels, for example to permit detection of a target nucleic acid molecule using the disclosed probes. In various applications, such as in situ hybridization procedures, a nucleic acid probe includes a label (e.g., a detectable label). A "detectable label" is a molecule or material that can be used to produce a detectable signal that indicates the presence or concentration of the probe (particularly the bound or hybridized probe) in a sample. Thus, a labeled nucleic acid molecule provides an indicator of the presence or concentration of a target nucleic acid sequence (e.g., genomic target nucleic acid sequence) (to which the labeled uniquely specific nucleic acid molecule is bound or hybridized) in a sample. A label associated with one or more nucleic acid molecules (such as a probe generated by the disclosed methods) can be detected either directly or indirectly. A label can be detected by any known or yet to be discovered mechanism including absorption, emission and/or scattering of a photon (including radio frequency, microwave frequency, infrared frequency, visible frequency and ultraviolet frequency photons). Detectable labels include colored, fluorescent, phosphorescent and luminescent molecules and materials, catalysts (such as enzymes) that convert one substance into another substance to provide a detectable difference (such as by converting a colorless substance into a colored substance or vice versa, or by producing a precipitate or increasing sample turbidity), haptens that can be detected by antibody binding interactions, and paramagnetic and magnetic molecules or materials.

Particular examples of detectable labels include fluorescent molecules (or fluorochromes). Numerous fluorochromes are known to those of skill in the art, and can be selected, for example from Life Technologies (formerly Invitrogen), e.g., see, The Handbook—A Guide to Fluorescent Probes and Labeling Technologies. Examples of particular fluorophores that can be attached (for example, chemically conjugated) to a nucleic acid molecule (such as a uniquely specific binding region) are provided in U.S. Pat. No. 5,866,366 to Nazarenko et al., such as 4-acetamido-4'-isothiocyanatostilbene-2,2' disulfonic acid, acridine and derivatives such as acridine and acridine isothiocyanate, 5-(2'-aminoethyl) aminonaphthalene-1-sulfonic acid (EDANS), 4-amino-N-[3 vinylsulfonyl)phenyl]naphthalimide-3,5 disulfonate (Lucifer Yellow VS), N-(4-anilino-1-naphthyl)maleimide, antllranilamide, Brilliant Yellow, coumarin and derivatives such as coumarin, 7-amino-4-methylcoumarin (AMC, Coumarin 120), 7-amino-4-trifluoromethylcouluarin (Coumarin 151); cyanosine; 4',6-diarninidino-2-phenylindole (DAPI); 5',5"dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulforlic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4, 6dic11lorotriazin-2-yDarninofluorescein (DTAF), 2 '7'dimethoxy-4'5 '-dichloro-6-carboxyfluorescein (JOE), fluorescein, fluorescein isothiocyanate (FITC), and QFITC Q(RITC); 2 ', 7'-difluorofluorescein (OREGON GREEN®); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, rhodamine green, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives. Other suitable fluorophores include thiol-reactive europium chelates which emit at approximately 617 mn (Heyduk and Heyduk, Analyt. Biochem. 248:216-27, 1997; J. Biol. Chem. 274:3315-22, 1999), as well as GFP, Lissamine™, diethylaminocoumarin, fluorescein chlorotriazinyl, naphthofluorescein, 4,7-dichlororhodamine and xanthene (as described in U.S. Pat. No. 5,800,996 to Lee et al.) and derivatives thereof. Other fluorophores known to those skilled in the art can also be used, for example those available from Life Technologies (Invitrogen;

Molecular Probes (Eugene, Oreg.)) and including the ALEXA FLUOR® series of dyes (for example, as described in U.S. Pat. Nos. 5,696,157, 6, 130, 101 and 6,716,979), the BODIPY series of dyes (dipyrrometheneboron difluoride dyes, for example as described in U.S. Pat. Nos. 4,774,339, 5,187,288, 5,248,782, 5,274,113, 5,338,854, 5,451,663 and 5,433,896), Cascade Blue (an amine reactive derivative of the sulfonated pyrene described in U.S. Pat. No. 5,132,432) and Marina Blue (U.S. Pat. No. 5,830,912).

In addition to the fluorochromes described above, a fluorescent label can be a fluorescent nanoparticle, such as a semiconductor nanocrystal, e.g., a QUANTUM DOT™ (obtained, for example, from Life Technologies (Quantum-Dot Corp, Invitrogen Nanocrystal Technologies, Eugene, Oreg.); see also, U.S. Pat. Nos. 6,815,064; 6,682,596; and 6,649, 138). Semiconductor nanocrystals are microscopic particles having size-dependent optical and/or electrical properties. When semiconductor nanocrystals are illuminated with a primary energy source, a secondary emission of energy occurs of a frequency that corresponds to the handgap of the semiconductor material used in the semiconductor nanocrystal. This emission can be detected as colored light of a specific wavelength or fluorescence. Semiconductor nanocrystals with different spectral characteristics are described in e.g., U.S. Pat. No. 6,602,671. Semiconductor nanocrystals that can be coupled to a variety of biological molecules (including dNTPs and/or nucleic acids) or substrates by techniques described in, for example, Bruchez et al., Science 281 :20132016, 1998; Chan et al., Science 281:2016-2018, 1998; and U.S. Pat. No. 6,274,323. Formation of semiconductor nanocrystals of various compositions are disclosed in, e.g., U.S. Pat. Nos. 6,927,069; 6,914,256; 6,855,202; 6,709,929; 6,689,338; 6,500,622; 6,306,736; 6,225,198; 6,207,392; 6,114,038; 6,048,616; 5,990,479; 5,690,807; 5,571,018; 5,505,928; 5,262,357 and in U.S. Patent Puhlication No. 2003/0165951 as well as PCT Puhlication No. 99/26299 (puhlished May 27, 1999). Separate populations of semiconductor nanocrystals can be produced that are identifiable based on their different spectral characteristics. For example, semiconductor nanocrystals can be produced that emit light of different colors hased on their composition, size or size and composition. For example, quantum dots that emit light at different wavelengths based on size (565 mn, 655 mn, 705 mn, or 800 mn emission wavelengths), which are suitable as fluorescent labels in the probes disclosed herein are available from Life Technologies (Carlshad, Calif.).

Additional labels include, for example, radioisotopes (such as H), metal chelates such as DOTA and DPTA chelates of radioactive or paramagnetic metal ions like $Gd^{3+}$, and liposomes.

Detectable labels that can be used with nucleic acid molecules also include enzymes, for example horseradish peroxidase, alkaline phosphatase, acid phosphatase, glucose oxidase, beta-galactosidase, beta-glucuronidase, or beta-lactamase.

Alternatively, an enzyme can be used in a metallographic detection scheme. For example, silver in situ hyhridization (SISH) procedures involve metallographic detection schemes for identification and localization of a hybridized genomic target nucleic acid sequence. Metallographic detection methods include using an enzyme, such as alkaline phosphatase, in combination with a water-soluble metal ion and a redox-inactive substrate of the enzyme. The substrate is converted to a redox-active agent by the enzyme, and the redoxactive agent reduces the metal ion, causing it to form a detectable precipitate. (See, for example, U.S. Patent Application Puhlication No. 2005/0100976, PCT Publication No. 2005/003777 and U.S. Patent Application Publication No. 2004/ 0265922). Metallographic detection methods also include using an oxido-reductase enzyme (such as horseradish peroxidase) along with a water soluble metal ion, an oxidizing agent and a reducing agent, again to form a detectable precipitate. (See, for example, U.S. Pat. No. 6,670,113).

Probes made using the disclosed methods can be used for nucleic acid detection, such as ISH procedures (for example, fluorescence in situ hybridization (FISH), chromogenic in situ hybridization (CISH) and silver in situ hybridization (SISH)) or comparative genomic hybridization (CGH).

In situ hybridization (ISH) involves contacting a sample containing target nucleic acid sequence (e.g., genomic target nucleic acid sequence) in the context of a metaphase or interphase chromosome preparation (such as a cell or tissue sample mounted on a slide) with a labeled probe specifically hybridizable or specific for the target nucleic acid sequence (e.g., genomic target nucleic acid sequence). The slides are optionally pretreated, e.g., to remove paraffin or other materials that can interfere with uniform hybridization. The sample and the probe are both treated, for example by heating to denature the double stranded nucleic acids. The probe (formulated in a suitable hybridization buffer) and the sample arc combined, under conditions and for sufficient time to permit hybridization to occur (typically to reach equilibrium). The chromosome preparation is washed to remove excess probe, and detection of specific labeling of the chromosome target is performed using standard techniques.

For example, a biotinylated probe can be detected using fluorescein-labeled avidin or avidin-alkaline phosphatase. For fluorochrome detection, the fluorochrome can be detected directly, or the samples can be incubated, for example, with fluorescein isothiocyanate (FITC)-conjugated avidin. Amplification of the FITC signal can be effected, if necessary, by incubation with biotin-conjugated goat antiavidin antibodies, washing and a second incubation with FITC-conjugated avidin. For detection by enzyme activity, samples can be incubated, for example, with streptavidin, washed, incubated with biotin-conjugated alkaline phosphatase, washed again and pre-equilibrated (e.g., in alkaline phosphatase (AP) buffer). For a general description of in situ hybridization procedures, see, e.g., U.S. Pat. No. 4,888,278.

Numerous procedures for FISH, CISH, and SISH are known in the art. For example, procedures for performing FISH are described in U.S. Pat. Nos. 5,447,841; 5,472,842; and 5,427,932; and for example, in Pirlkel et al., Proc. Natl. Acad. Sci. 83:2934-2938, 1986;

Pinkel et al., Proc. Natl. Acad. Sci. 85:9138-9142, 1988; and Lichter et al., Proc. Natl. Acad. Sci. 85:9664-9668, 1988. CISH is described in, e.g., Tanner et al., Am. .1. Pathol. 157:1467-1472, 2000 and U.S. Pat. No. 6,942,970. Additional detection methods are provided in U.S. Pat. No. 6,280,929.

Numerous reagents and detection schemes can be employed in conjunction with FISH, CISH, and SISH procedures to improve sensitivity, resolution, or other desirable properties. As discussed above probes labeled with fluorophores (including fluorescent dyes and QUANTUM DOTS®) can be directly optically detected when performing FISH. Alternatively, the probe can be labeled with a nonfluorescent molecule, such as a hapten (such as the following non-limiting examples: biotin, digoxigenin, DNP, and various oxazoles, pyrrazoles, thiazoles, nitroaryls, benzofurazans, triterpenes, ureas, thioureas, rotenones, coumarin, courmarin-based compounds, Podophyllotoxin, Podophyllotoxin-based compounds, and combinations thereof), ligand or other indirectly detectable moiety. Probes labeled with such non-fluorescent molecules (and the target nucleic acid sequences to which they bind) can then be detected by contacting the sample (e.g., the cell or tissue sample to which the probe is bound) with a labeled detection reagent, such as an antibody (or receptor, or other specific binding partner) specific for the chosen hapten or ligand. The detection reagent can be labeled with a fluorophore (e.g., QUANTUM DOT®) or with another indirectly detectable moiety, or can be contacted with one or more additional specific binding agents (e.g., secondary or specific antibodies), which can be labeled with a fluorophore.

In other examples, the probe, or specific binding agent (such as an antibody, e.g., a primary antibody, receptor or other binding agent) is labeled with an enzyme that is capable of converting a fluorogenic or chromogenic composition into a detectable fluorescent, colored or otherwise detectable signal (e.g., as in deposition of detectable metal particles in SISH). As indicated above, the enzyme can be attached directly or indirectly via a linker to the relevant probe or detection reagent. Examples of suitable reagents (e.g., binding reagents) and chemistries (e.g., linker and attachment chemistries) are described in U.S. Patent Application Publication Nos. 2006/0246524; 2006/0246523, and 2007/01 17153.

It will be appreciated by those of skill in the art that by appropriately selecting labelled probe-specific binding agent pairs, multiplex detection schemes can be produced to facilitate detection of multiple target nucleic acid sequences (e.g., genomic target nucleic acid sequences) in a single assay (e.g., on a single cell or tissue sample or on more than one cell or tissue sample). For example, a first probe that corresponds to a first target sequence can be labelled with a first hapten, such as biotin, while a second probe that corresponds to a second target sequence can be labelled with a second hapten, such as DNP. Following exposure of the sample to the probes, the bound probes can be detected by contacting the sample with a first specific binding agent (in this case avidin labelled with a first fluorophore, for example, a first spectrally distinct QUANTUM DOT®, e.g., that emits at 585 mn) and a second specific binding agent (in this case an anti-DNP antibody, or antibody fragment, labelled with a second fluorophore (for example, a second spectrally distinct QUANTUM DOT®, e.g., that emits at 705 mn). Additional probes/binding agent pairs can be added to the multiplex detection scheme using other spectrally distinct fluorophores. Numerous variations of direct, and indirect (one step, two step or more) can be envisioned, all of which are suitable in the context of the disclosed probes and assays.

Probes typically comprise single-stranded nucleic acids of between 10 to 1000 nucleotides in length, for instance of between 10 and 800, more preferably of between 15 and 700, typically of between 20 and 500. Primers typically are shorter single-stranded nucleic acids, of between 10 to 25 nucleotides in length, designed to perfectly or almost perfectly match a nucleic acid of interest, to be amplified. The probes and primers are "specific" to the nucleic acids they hybridize to, i.e. they preferably hybridize under high stringency hybridization conditions (corresponding to the highest melting temperature Tm, e.g., 50% formamide, 5× or 6×SCC. SCC is a 0.15 M NaCl, 0.015 M Na-citrate).

The nucleic acid primers or probes used in the above amplification and detection method may be assembled as a kit. Such a kit includes consensus primers and molecular probes. A preferred kit also includes the components necessary to determine if amplification has occurred. The kit may also include, for example, PCR buffers and enzymes; positive control sequences, reaction control primers; and instructions for amplifying and detecting the specific sequences.

In a particular embodiment, the methods of the invention comprise the steps of providing total RNAs extracted from cumulus cells and subjecting the RNAs to amplification and hybridization to specific probes, more particularly by means of a quantitative or semi-quantitative RT-PCR.

In another preferred embodiment, the expression level is determined by DNA chip analysis. Such DNA chip or nucleic acid microarray consists of different nucleic acid probes that are chemically attached to a substrate, which can be a microchip, a glass slide or a microsphere-sized bead. A microchip may be constituted of polymers, plastics, resins, polysaccharides, silica or silica-based materials, carbon, metals, inorganic glasses, or nitrocellulose. Probes comprise nucleic acids such as cDNAs or oligonucleotides that may be about 10 to about 60 base pairs. To determine the expression level, a sample from a test subject, optionally first subjected to a reverse transcription, is labelled and contacted with the microarray in hybridization conditions, leading to the formation of complexes between target nucleic acids that are complementary to probe sequences attached to the microarray surface. The labelled hybridized complexes are then detected and can be quantified or semi-quantified. Labelling may be achieved by various methods, e.g. by using radioactive or fluorescent labelling. Many variants of the microarray hybridization technology are available to the man skilled in the art (see e.g. the review by Hoheisel, Nature Reviews, Genetics, 2006, 7:200-210).

Expression level of a gene may be expressed as absolute expression level or normalized expression level. Typically, expression levels are normalized by correcting the absolute expression level of a gene by comparing its expression to the expression of a gene that is not a relevant for determining the cancer stage of the patient, e.g., a housekeeping gene that is constitutively expressed. Suitable genes for normalization include housekeeping genes such as the actin gene ACTB, ribosomal 18S gene, GUSB, PGK1 and TFRC. This normalization allows the comparison of the expression level in one sample, e.g., a patient sample, to another sample, or between samples from different sources.

Predetermined reference values used for comparison may comprise "cut-off" or "threshold" values that may be determined as described herein. Each reference ("cut-off") value for each gene of interest may be predetermined by carrying out a method comprising the steps of
a) providing a collection of tumor tissue samples from patients suffering of cancer;
b) determining the expression level of the gene for each tumour tissue sample contained in the collection provided at step a);
c) ranking the tumor tissue samples according to said expression level
d) classifying said tumour tissue samples in pairs of subsets of increasing, respectively decreasing, number of members ranked according to their expression level,
e) providing, for each tumour tissue sample provided at step a), information relating to the actual clinical outcome for the corresponding cancer patient (i.e. the duration of the disease-free survival (DFS) or the overall survival (OS) or both);
f) for each pair of subsets of tumour tissue samples, obtaining a Kaplan Meier percentage of survival curve;
g) for each pair of subsets of tumour tissue samples calculating the statistical significance (p value) between both subsets
h) selecting as reference value for the expression level, the value of expression level for which the p value is the smallest.

For example the expression level of a gene X has been assessed for 100 cancer samples of 100 patients. The 100 samples are ranked according to their expression level. Sample 1 has the best expression level and sample 100 has the worst expression level. A first grouping provides two subsets: on one side sample Nr 1 and on the other side the 99 other samples. The next grouping provides on one side samples 1 and 2 and on the other side the 98 remaining samples etc., until the last grouping: on one side samples 1 to 99 and on the other side sample Nr 100. According to the information relating to the actual clinical outcome for the corresponding cancer patient, Kaplan Meier curves are prepared for each of the 99 groups of two subsets. Also for each of the 99 groups, the p value between both subsets was calculated.

The reference value is selected such as the discrimination based on the criterion of the minimum p value is the strongest. In other terms, the expression level corresponding to the boundary between both subsets for which the p value is minimum is considered as the reference value. It should be noted that the reference value is not necessarily the median value of expression levels.

In routine work, the reference value (cut-off value) may be used in the present method to discriminate tumour samples and therefore the corresponding patients.

Kaplan-Meier curves of percentage of survival as a function of time are commonly to measure the fraction of patients living for a certain amount of time after treatment and are well known by the man skilled in the art.

The man skilled in the art also understands that the same technique of assessment of the expression level of a gene should of course be used for obtaining the reference value and thereafter for assessment of the expression level of a gene of a patient subjected to the method of the invention.

Such predetermined reference values of expression level may be determined for any gene defined above As patients with High (Hi) or Low (Lo) adaptive immune gene signature have very different clinical outcome and very different survival time (strong prognostic value of the adaptive immune gene signature), it is necessary to stratify patients based on this adaptive immune gene signature (Hi or Lo) in order to predict the patients who will benefit from cancer treatment. Comparison of patient groups with similar adaptive immune gene signature, Hi OR Lo, will allow to detect and predict the patients who will significantly respond to the cancer treatment. For example FIG. 4 illustrates stage IV colorectal cancer patients, where patient with a "Hi" adaptive immune gene signature have prolonged survival and do not need chemotherapy treatment (no benefit from chemotherapy treatment). A significant benefic effect of chemotherapy treatment can be observed in patients with a "Lo" adaptive immune gene signature. FIG. 2 illustrates stages I/III colorectal cancer patients, where patient with a "Lo" adaptive immune gene signature have a poor survival and do not benefit from chemotherapy treatment, whereas patients with a "Hi" adaptive immune gene signature have an improved outcome when they received chemotherapy treatment. Similarly to FIG. 2, FIG. 6 illustrates stages II colorectal cancer patients, where patient with a "Lo" adaptive immune gene signature have a poor survival and do not benefit from chemotherapy treatment, whereas patients with a "Hi" adaptive immune gene signature have an improved outcome when they received chemotherapy treatment. Accordingly, the method of the present invention may be suitable to discriminate patients between 2 groups: a first group of patients as "bad responders" (i.e. the treatment will have a limited (or moderate) impact on their survival) and a second group as "good responders" (i.e. the treatment will have a significant impact on their survival).

Accordingly a further aspect of the invention relates to a method for determining whether a patient suffering from a cancer will respond to a treatment comprising i) determining in a tumor sample obtained from the patient the gene expression level of at least 7 genes selected from the group consisting of CCR2, CD3D, CD3E, CD3G, CD8A, CXCL10, CXCL11, GZMA, GZMB, GZMK, GZMM, IL15, IRF1, PRF1, STAT1, CD69, ICOS, CXCR3, STAT4, CCL2, and TBX21 ii) comparing every expression level determined at step i) with their predetermined reference value and iii) concluding that the patient will significantly respond to the treatment when all expression levels determined at step i) are higher or lower than their predetermined reference values.

Accordingly a further aspect of the invention relates to a method for determining whether a patient suffering from a cancer will respond to a treatment comprising i) determining in a tumor sample obtained from the patient the gene expression level of CCR2, CD3D, CD3E, CD3G, CD8A, CXCL10, CXCL11, GZMA, GZMB, GZMK, GZMM, IL15, IRF1, PRF1, STAT1, CD69, ICOS, CXCR3, STAT4, CCL2, and TBX21 ii) comparing every expression level determined at step i) with their predetermined reference value and iii) concluding that the patient will significantly respond to the treatment when all expression levels determined at step i) are higher or lower than their predetermined reference values.

In a particular embodiment, the invention relates to a method for determining whether a patient suffering from a non metastatic colorectal cancer will respond to a treatment comprising i) determining in a tumor sample obtained from the patient the gene expression level of CCR2, CD3D, CD3E, CD3G, CD8A, CXCL10, CXCL11, GZMA, GZMB, GZMK, GZMM, IL15, IRF1, PRF1, STAT1, CD69, 1COS, CXCR3, STAT4, CCL2, and TBX21 ii) comparing every expression level determined at step i) with their predetermined reference value and iii) concluding that the patient will significantly respond to the treatment when all expression levels determined at step i) are higher than their predetermined reference values, or concluding that the patient will not significantly respond to the treatment when all expression levels determined at step i) are lower than their predetermined reference values.

Intermediate conclusions may also be provided when at least one gene is higher than its corresponding predetermined reference value. Every time that the expression level of a gene is higher than its predetermined reference value, better will be the response of the patient to the treatment.

The method as above described is particularly suitable for early advanced cancer patients (stage II according to the TNM classification) for whom there are not established guidelines for the treatment. The method as above described will full fill the need by providing a reliant tool for determining whether a patient with a non metastatic patient could benefit of a treatment.

In a particular embodiment, the invention relates to a method for determining whether a patient with a metastatic colorectal cancer will respond to a treatment comprising i) determining in a tumor sample obtained from the patient the gene expression level of CCR2, CD3D, CD3E, CD3G, CD8A, CXCL10, CXCL11, GZMA, GZMB, GZMK, GZMM, IL15, IRF1, PRF1, STAT1, CD69, ICOS, CXCR3, STAT4, CCL2, and TBX21 comparing every expression level determined at step i) with their predetermined reference value and iii) concluding that the patient will significantly respond to the treatment when all expression levels determined at step i) are lower than their predetermined reference values, or concluding that the patient will not significantly respond to the treatment when all expression levels determined at step i) are higher than their predetermined reference values.

Intermediate conclusions may also be provided when at least one gene is lower than its corresponding predetermined reference value. Every time that the expression level of a gene is lower than its predetermined reference value, better will be the response of the patient to the treatment.

In a particular embodiment, the invention relates to a method for determining whether a patient with a non metastatic lung cancer will respond to a treatment comprising i) determining in a tumor sample obtained from the patient the gene expression level of CCR2, CD3D, CD3E, CD3G, CD8A, CXCL 10, CXCL 11, GZMA, GZMB, GZMK, GZMM, IL15, IRF1, PRF1, STAT1, CD69, ICOS, CXCR3, STAT4, CCL2, and TBX21 ii) comparing every expression level determined at step i) with their predetermined reference value and iii) concluding that the patient will significantly respond to the treatment when all expression levels determined at step i) are lower than their predetermined reference values, or concluding that the patient will not significantly respond to the treatment when all expression levels determined at step i) are higher than their predetermined reference values.

In a particular embodiment, the invention relates to a method for determining whether a patient with a metastatic ovarian cancer will respond to a treatment comprising i) determining in a tumor sample obtained from the patient the gene expression level of CCR2, CD3D, CD3E, CD3G, CD8A, CXCL10, CXCL11, GZMA, GZMB, GZMK, GZMM, IL15, IRF1, PRF1, STAT1, CD69, ICOS, CXCR3, STAT4, CCL2, and TBX21 ii) comparing every expression level determined at step i) with their predetermined reference value and iii) concluding that the patient will significantly respond to the treatment when all expression levels determined at step i) are higher than their predetermined reference values, or concluding that the patient will not significantly respond to the treatment when all expression levels determined at step i) are lower than their predetermined reference values.

The treatment may consist of radiotherapy, chemotherapy or immunotherapy. The treatment may consist of an adjuvant therapy (i.e. treatment after chirurgical resection of the primary tumor) of a neoadjuvant therapy (i.e. treatment before chirurgical resection of the primary tumor).

The term "chemotherapeutic agent" refers to all chemical compounds that are effective in inhibiting tumor growth. Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaorarnide and trimethylolomelamine; acetogenins (especially bullatacin and bullatacinone); a carnptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estrarnustine, ifosfamide, mechlorethamine, mechlorethamine oxide hydrochloride, melphalan, novembichin, phenesterine, prednimus tine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin (11 and calicheamicin 211, see, e.g., Agnew Chem Intl. Ed. Engl. 33:183-186 (1994); dynemicin, including dynemicin A; an esperamicin; as well as neocarzinostatin chromophore and related chromoprotein enediyne antiobiotic chromomophores), aclacinomysins, actinomycin, authramycin, azaserine, bleomycins, cactinomycin, carabicin, canninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idanrbicin, marcellomycin, mitomycins, mycophenolic acid, nogalarnycin, olivomycins, peplomycin, potfiromycin, puromycin, quelamycin, rodorubicin, streptomgrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabinc, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid;

aceglatone; aldophospharnide glycoside; aminolevulinic acid; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pento statin; phenamet; pirarubicin; podophyllinic acid; 2-ethylhydrazide; procarbazine; PSK®; razoxane; rhizoxin; sizofiran; spirogennanium; tenuazonic acid; triaziquone; 2,2 ',2"-trichlorotriethylamine; trichothecenes (especially T-2 toxin, vcrracurin A, roridinA and anguidine); urethan; vindesine; dacarbazine; mannomustine; mitobromtol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-1 1; topoisomerase inhibitor RFS 2000; difluoromethylornithine (DMFO); retinoic acid; capecitabine; and phannaceutically acceptable salts, acids or derivatives of any of the above. Also included in this definition are antihormonal agents that act to regulate or inhibit honnone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and phannaceutically acceptable salts, acids or derivatives of any of the above.

The term "immunotherapeutic agent," as used herein, refers to a compound, composition or treatment that indirectly or directly enhances, stimulates or augments the body's immune response against cancer cells and/or that lessens the side effects of other anticancer therapies. Immunotherapy is thus a therapy that directly or indirectly stimulates or enhances the immune system's responses to cancer cells and/or lessens the side effects that may have been caused by other anti-cancer agents. Immunotherapy is also referred to in the art as immunologic therapy, biological therapy biological response modifier therapy and biotherapy. Examples of common immunotherapeutic agents known in the art include, but are not limited to, cytokines, cancer vaccines, monoclonal antibodies and non-cytokine adjuvants. Alternatively the immunotherapeutic treatment may consist of administering the patient with an amount of immune cells (T cells, NK, cells, dendritic cells, B cells . . . ).

Immunotherapeutic agents can be non-specific, i.e. boost the immune system generally so that it becomes more effective in fighting the growth and/or spread of cancer cells, or they can be specific, i.e. targeted to the cancer cells themselves immunotherapy regimens may combine the use of non-specific and specific immunotherapeutic agents.

Non-specific immunotherapeutic agents are substances that stimulate or indirectly augment the immune system. Non-specific immunotherapeutic agents have been used alone as the main therapy for the treatment of cancer, as well as in addition to a main therapy, in which case the non-specific immunotherapeutic agent functions as an adjuvant to enhance the effectiveness of other therapies (e.g. cancer vaccines). Non-specific immunotherapeutic agents can also function in this latter context to reduce the side effects of other therapies, for example, bone marrow suppression induced by certain chemotherapeutic agents. Non-specific immunotherapeutic agents can act on key immune system cells and cause secondary responses, such as increased production of cytokines and immunoglobulins. Alternatively, the agents can themselves comprise cytokines. Non-specific immunotherapeutic agents are generally classified as cytokines or non-cytokine adjuvants.

A number of cytokines have found application in the treatment of cancer either as general non-specific immunotherapies designed to boost the immune system, or as adjuvants provided with other therapies. Suitable cytokines include, but are not limited to, interferons, interleukins and colony-stimulating factors.

Interferons (IFNs) contemplated by the present invention include the common types of IFNs, IFN-alpha (IFN-α), IFN-beta (IFN-beta) and IFN-gamma (IFN-γ). IFNs can act directly on cancer cells, for example, by slowing their growth, promoting their development into cells with more normal behaviour and/or increasing their production of antigens thus making the cancer cells easier for the immune system to recognise and destroy. IFNs can also act indirectly on cancer cells, for example, by slowing down angiogenesis, boosting the immune system and/or stimulating natural killer (NK) cells, T cells and macrophages. Recombinant IFN-alpha is available commercially as ROFERON® (Roche Pharmaceuticals) and INTRON® A (Schering Corporation). The use of IFN-alpha, alone or in combination with other immunotherapeutics or with chemotherapeutics, has shown efficacy in the treatment of various cancers including melanoma (including metastatic melanoma), renal cancer (including metastatic renal cancer), breast cancer, prostate cancer, and cervical cancer (including metastatic cervical cancer).

Interleukins contemplated by the present invention include IL-2, IL-4, 1L-11 and IL-12. Examples of commercially available recombinant interleukins include Proleukin® (IL-2; Chiron Corporation) and Neumega® (IL-12; Wyeth Pharmaceuticals). Zymogenetics, Inc. (Seattle, Wash.) is currently testing a recombinant form of IL-21, which is also contemplated for use in the combinations of the present invention. Interleukins, alone or in combination with other immunotherapeutics or with chemotherapeutics, have shown efficacy in the treatment of various cancers including renal cancer (including metastatic renal cancer), melanoma (including metastatic melanoma), ovarian cancer (including recurrent ovarian cancer), cervical cancer (including metastatic cervical cancer), breast cancer, colorectal cancer, lung cancer, brain cancer, and prostate cancer.

Interleukins have also shown good activity in combination with IFN-a in the treatment of various cancers (Negrier et al., Ann Oncol. 2002 13(9):1460-8; Touranietal, J Clin Oncol. 2003 21(21):398794).

Colony-stimulating factors (CSFs) contemplated by the present invention include granulocyte colony stimulating factor (G-CSF or filgrastim), granulocyte-macrophage colony stimulating factor (GM-CSF or sargramostim) and erythropoietin (epoetin alfa, darbepoietin). Treatment with one or more growth factors can help to stimulate the generation of new blood cells in patients undergoing traditional chemotherapy. Accordingly, treatment with CSFs can be helpful in decreasing the side effects associated with chemotherapy and can allow for higher doses of chemotherapeutic agents to be used. Various-recombinant colony stimulating factors are available commercially, for example, Neupogen® (G-CSF; Amgen), Neulasta (pelfilgrastim; Amgen), Leukine (GM-CSF; Berlex), Procrit (erythropoietin; Ortho Biotech), Epogen (erythropoietin; Amgen), Arnesp (erytropoietin). Colony stimulating factors have shown efficacy in the treatment of cancer, including melanoma, colorectal cancer (including metastatic colorectal cancer), and lung cancer.

Non-cytokine adjuvants suitable for use in the combinations of the present invention include, but are not limited to, Levamisole, alum hydroxide (alum), bacillus Calmette-Guerin (ACG), incomplete Freund's Adjuvant (IFA), QS-21, DETOX, Keyhole limpet hemocyanin (KLH) and dinitrophenyl (DNP). Non-cytokine adjuvants in combination with other immuno-and/or chemotherapeutics have demonstrated efficacy against various cancers including, for example, colon cancer and colorectal cancer (Levimasole); melanoma (BCG and QS-21); renal cancer and bladder cancer (BCG).

In addition to having specific or non-specific targets, immunotherapeutic agents can be active, i.e. stimulate the body's own immune response, or they can be passive, i.e. comprise immune system components that were generated external to the body.

Passive specific immunotherapy typically involves the use of one or more monoclonal antibodies that are specific for a particular antigen found on the surface of a cancer cell or that are specific for a particular cell growth factor. Monoclonal antibodies may be used in the treatment of cancer in a number of ways, for example, to enhance a subject's immune response to a specific type of cancer, to interfere with the growth of cancer cells by targeting specific cell growth factors, such as those involved in angiogenesis, or by enhancing the delivery of other anticancer agents to cancer cells when linked or conjugated to agents such as chemotherapeutic agents, radioactive particles or toxins.

Monoclonal antibodies currently used as cancer immunotherapeutic agents that are suitable for inclusion in the combinations of the present invention include, but are not limited to, rituximab (Rituxan®), trastuzumab (Herceptin®), ibritumomab tiuxetan (Zevalin®), tositumomab (Bexxar®), cetuximab (C-225, Erbitux®), bevacizumab (Avastin®), gemtuzumab ozogamicin (Mylotarg®), alemtuzumab (Campath®), and BL22. Monoclonal antibodies are used in the treatment of a wide range of cancers including breast cancer (including advanced metastatic breast cancer), colorectal cancer (including advanced and/or metastatic colorectal cancer), ovarian cancer, lung cancer, prostate cancer, cervical cancer, melanoma and brain tumours.

Other examples include antibodies specific a co-stimulatory molecule. Co-stimulatory molecules include, for example B7-1/CD80, CD28, B7-2/CD86, CTLA-4, B7-HI/PD-L1, Gi24/Dies 1/VISTA, B7-H2, ICOS, B7-H3 PD-1, B7-H4, PD-L2/B7-DC, B7-H6, PDCD6, BTLA, 4-1 BB/TNFRSF9/CD137, CD40 Ligand/TNFSFS, 4-IBB Ligand/TNFSF9 GITR/TNFRSF18, HVEM/TNFRSF14, CD27/TNFRSF7, LIGHT/TNFSF14, CD27 Ligand/TNFSF7, OX40/TNFRSF4, CD30/TNFRSF8, OX40 Ligand/TNFSF4, CD30 Ligand/TNFSF8, TACl/TNFRSF13B, CD40/TNFRSF5, 2B4/CD244/SLAMF4 CD84/SLAMF5, BLAME/SLAMF8, CD229/SLAMF3, CD2CRACC/SLAMF7, CD2F-10/SLAMF9 NTB-A/SLAMF6, CD48/SLAMF2, SLAM/CD 150, CD58/LFA-3, CD2 Ikaros, CD53 Integrin alpha 4/CD49d, CD82/Kai-1 Integrin alpha 4 beta 1, CD90/Thyl Integrin alpha 4 beta 7/LPAM-1, CD96 LAG-3, CD160 LMIR1/CD300A, CRTAM TCL1A, DAP 12 TCL1B, Dectin-1/CLEC7A TIM-1/KIM-1/HAVCR, DPPIV/CD26 TIM-4, EphB6 TSLP, HLA Class I TSLP R, HLA-DR. In particular, the antibody is selected from the group consisting of anti-CTLA4 antibodies (e.g. Ipilimumab), anti-PD1 antibodies, anti-PDL1 antibodies, anti-TTMP3 antibodies, anti-LAG3 antibodies, anti-B7H3 antibodies, anti-B7H4 antibodies anti-TREM antibodies, anti-BTLA antibodies, anti-LIGHT antibodies or anti-B7H6 antibodies.

Monoclonal antibodies can be used alone or in combination with other immunotherapeutic agents or chemotherapeutic agents.

Active specific immunotherapy typically involves the use of cancer vaccines. Cancer vaccines have been developed that comprise whole cancer cells, parts of cancer cells or one or more antigens derived from cancer cells. Cancer vaccines, alone or in combination with one or more immuno- or chemotherapeutic agents are being investigated in the treatment of several types of cancer including melanoma, renal cancer, ovarian cancer, breast cancer, colorectal cancer, and lung cancer. Non-specific immunotherapeutics are useful in combination with cancer vaccines in order to enhance the body's immune response.

The immunotherapeutic treatment may consist of an adoptive immunotherapy as described by Nicholas P. Restifo, Mark E. Dudley and Steven A. Rosenberg "Adoptive" immunotherapy for cancer: harnessing the T cell response, Nature Reviews Immunology, Volume 12, April 2012). In adoptive immunotherapy, the patient's circulating lymphocytes, or tumor infiltrated lymphocytes, are isolated in vitro, activated by lymphokines such as IL-2 or transuded with genes for tumor necrosis, and readministered (Rosenberg et al., 1988; 1989). The activated lymphocytes are most preferably be the patient's own cells that were earlier isolated from a blood or tumor sample and activated (or "expanded") in vitro. This form of immunotherapy has produced several cases of regression of melanoma and renal carcinoma.

The term "radiotherapeutic agent" as used herein, is intended to refer to any radiotherapeutic agent known to one of skill in the art to be effective to treat or ameliorate cancer, without limitation. For instance, the radiotherapeutic agent can be an agent such as those administered in brachytherapy or radionuclide therapy.

Such methods can optionally further comprise the administration of one or more additional cancer therapies, such as, but not limited to, chemotherapies, and/or another radiotherapy and/or another immunotherapy.

A further object of the invention relates to kits for performing the methods of the invention, wherein said kits comprise means for measuring the expression level of the 21 genes of the invention in the sample obtained from the patient.

Accordingly, the present invention also relates to a the kit of the invention comprising means for determining the expression level of least 7 genes selected from the group consisting of CCR2, CD3D, CD3E, CD3G, CD8A, CXCL10, CXCL11, GZMA, GZMB, GZMK, GZMM, IL15, IRF1, PRF1, STAT1, CD69, ICOS, CXCR3, STAT4, CCL2, and TBX21.

Accordingly, the present invention also relates to a the kit of the invention comprising means for determining the expression level of CCR2, CD3D, CD3E, CD3G, CD8A, CXCL10, CXCL11, GZMA, GZMB, GZMK, GZMM, IL15, IRF1, PRF1, STAT1, CD69, ICOS, CXCR3, STAT4, CCL2, and TBX21.

The kits may include probes, primers macroarrays or microarrays as above described. For example, the kit may comprise a set of probes as above defined, usually made of DNA, and that may be pre-labelled. Alternatively, probes may be unlabelled and the ingredients for labelling may be included in the kit in separate containers. The kit may further comprise hybridization reagents or other suitably packaged reagents and materials needed for the particular hybridization protocol, including solid-phase matrices, if applicable, and standards. Alternatively the kit of the invention may comprise amplification primers that may be pre-labelled or may contain an affinity purification or attachment moiety. The kit may further comprise amplification reagents and also other suitably packaged reagents and materials needed for the particular amplification protocol.

The invention will be further illustrated by the following figures and examples. However, these examples and figures should not be interpreted in any way as limiting the scope of the present invention.

FIGURES

Figure 7:
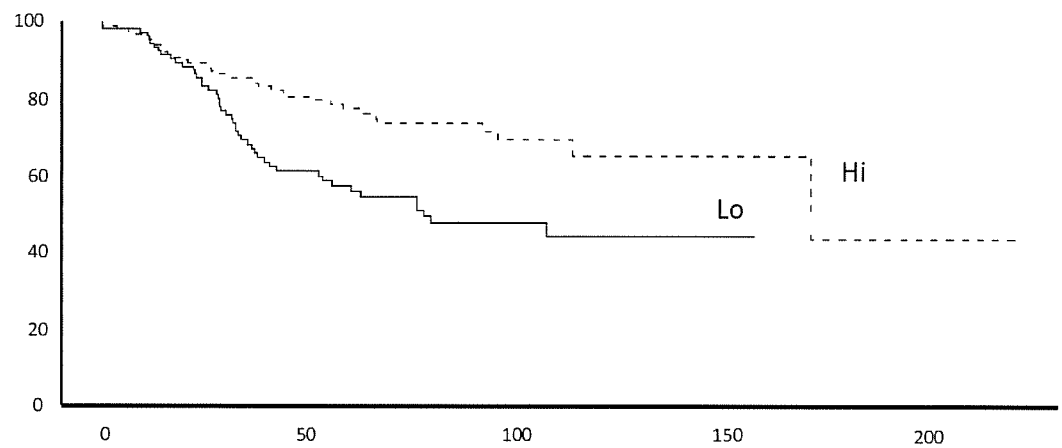

FIG. 7 shows the survival time (DFS in months) of a first cohort of patients ("IPC Series") having a breast cancer separated in 2 groups: "low levels" (Lo) for patient having a score of I0-I10 and "high levels" (Hi) for patients having a score of I11-I21 determined with 21 genes. The IPC series contained frozen tumor samples obtained from 266 early breast cancer patients who underwent initial surgery between 1992 and 2004. Gene expression data of 266 BCs were quantified by using whole genome DNA microarrays (HG-U133 plus 2.0, Affymetrix). (Sabatier R, Finelli P, Cervera N, Lambaudie E et al. A gene expression signature identifies two prognostic subgroups of basal breast cancer. Breast cancer Res Treat 2011 April; 126(2):407-20. PMID: 20490655).

Figure 8:
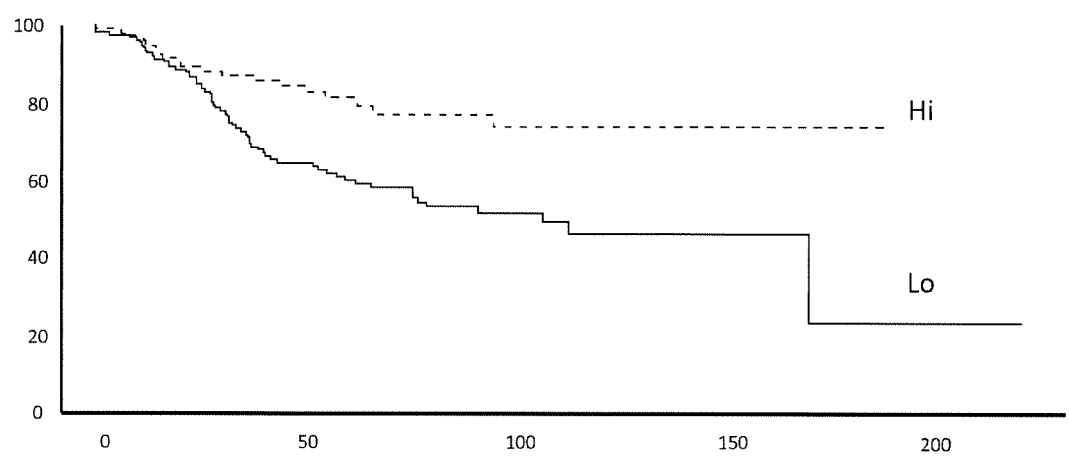

FIG. 8 shows the survival time (DFS in months) of a cohort of patients ("IPC Series") having a breast cancer separated in 2 groups: "low levels" (Lo) for patient having a score of I0-I3 and "high levels" (Hi) for patients having a score of I4-I7 determined with 7 genes (CCR2, GZMB, GZMK, ICOS, STAT1, STAT4, TBX21). The IPC series contained frozen tumor samples obtained from 266 early breast cancer patients who underwent initial surgery between 1992 and 2004. Gene expression data of 266 BCs were quantified by using whole genome DNA microarrays (HG-U133 plus 2.0, Affymetrix) (Sabatier R, Finelli P, Cervera N, Lambaudie E et al. A gene expression signature identifies two prognostic subgroups of basal breast cancer. Breast cancer Res Treat 2011 April; 126(2):407-20. PMID: 20490655).

Figure 9:
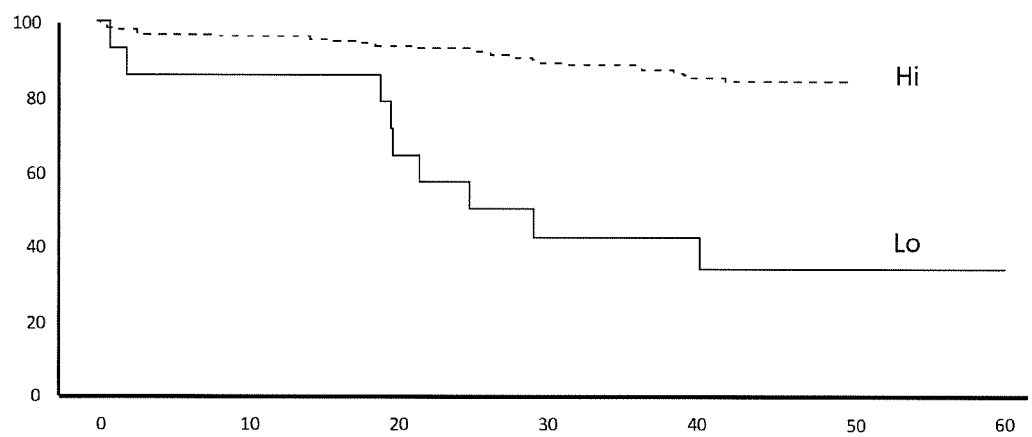

FIG. 9 shows the survival time (DFS in months) of a cohort of patients having a breast cancer separated in 2 groups: "low levels" (Lo) for patient having a score of I0-I9 and "high levels" (Hi) for patients having a score of I10-I18 determined with 18 genes (CCR2, CD3D, CD3E, CD3G, CD8A, CXCL10, CXCL11, GZMA, GZMB, GZMK, GZMM, IL15, IRF1, PRF1, CD69, ICOS, CXCR3, and STAT4). The cohort comprises 183 breast tumors from the Helsinki Univerisity Central Hospital with survival information (Heikkinen T, Greco D, Pelttari L M, Tommi ska J et al. variants on the promoter region of PTEN affect breast cancer progression and patient survival. Breast cancer Res 2011; 13(6):R130. PMID: 22171747). Total RNA was extracted from primary breast tumors of the 183 patients. The samples were processed and hybridized to Illumina HumanHT•12 v3 Expression BeadChips.

Figure 10:
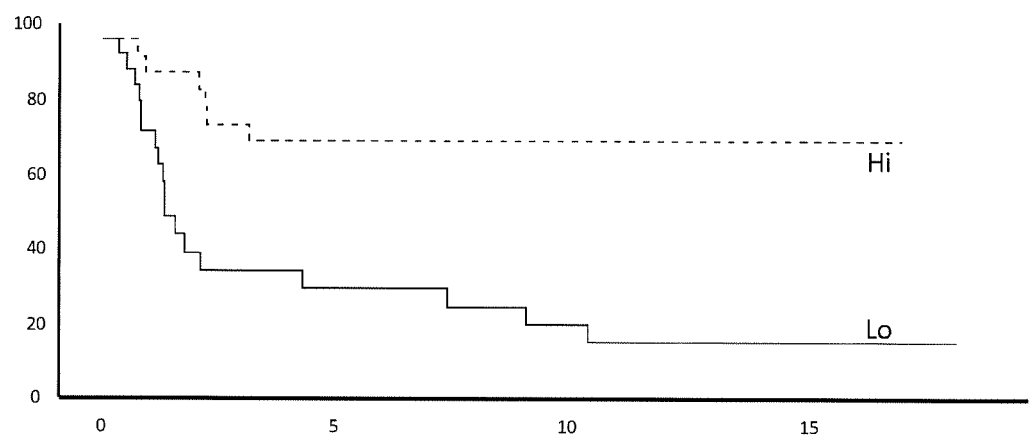

FIG. 10 shows the survival time (DFS in months) of a patients having a cervical cancer separated in 2 groups: "low levels" (Lo) for patient having a score of I0-I8 and "high levels" (Hi) for patients having a score of I9-I16 determined with 16 genes (CD3E, CD3G, CD8A, CXCL11, GZMA, GZMB, GZMK, GZMM, IL15, IRF1, CD69, ICOS, CXCR3, STAT4, CCL2, and TBX21). The cohort comprises 48 cervical cancers from women who were treated at the Innsbruck Medical University between 1990 and 2006. The samples were processed and hybridized to Illumina Infinium 27 k Human DNA methylation Beadchip v1.2. (Teschendorff A E, Jones A, Fiegl H, Sargent A et al. Epigenetic variability in cells of normal cytology is associated with the risk of future morphological transformation. Genome Med 2012 Mar. 27; 4(3):24. PMID: 22453031).

Figure 11:
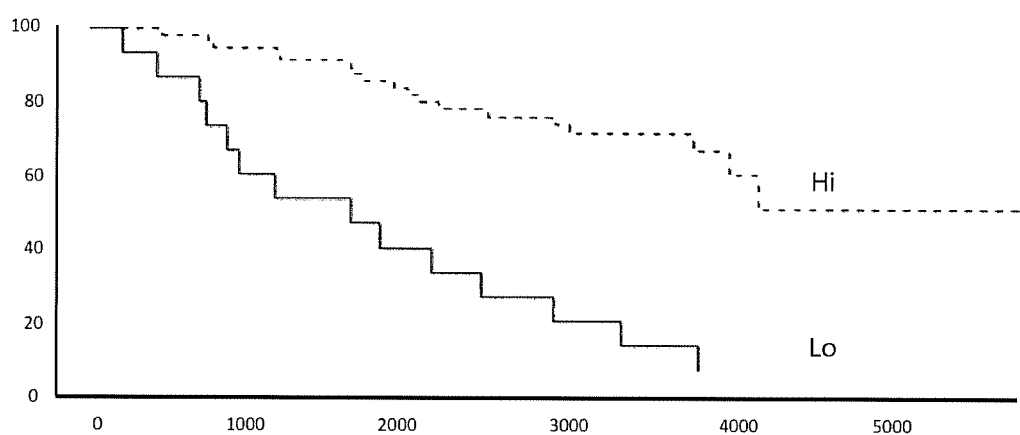

FIG. 11 shows the survival time (DFS in months) of a patients having a hepatocellular carcinoma separated in 2 groups: "low levels" (Lo) for patient having a score of I0-I7 and "high levels" (Hi) for patients having a score of I8-I14 determined with 14 genes (CCR2, CD3D, CD3E, CD8A, CXCL10, GZMA, GZMM, IL15, IRF1, PRF1, STAT1, CD69, CXCR3, and STAT4). The cohort comprises surgically resected 118 tumor tissues from patients with hepatocellular carcinoma (HCC) (Hoshida Y, Nijman S M, Kobayashi M, Chan J A et al. Integrative transcriptome analysis reveals common molecular subclasses of human hepatocellular carcinoma. cancer Res 2009 Sep 15; 69(18): 7385-92. PMID: 19723656.

Figure 12:
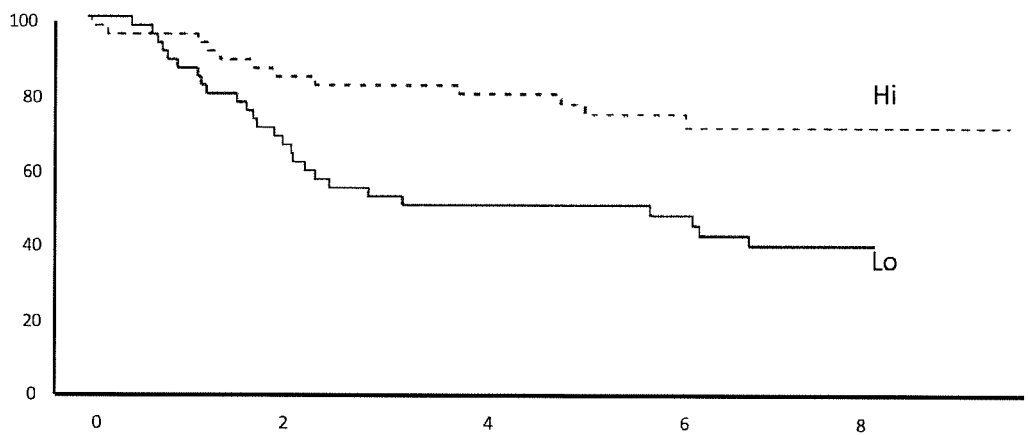

FIG. 12 shows the survival time (DFS in months) in patients having a lung cancer separated in 2 groups: "low levels" (Lo) for patient having a score of I0-I10 and "high levels" (Hi) for patients having a score of 111-121 determined with 21 genes. Gene expression profiling was conducted on mRNA isolated from 90 frozen JBR.10 tumor samples (either from patients under observation [OBS], or treated with adjuvant cisplatin/vinorelbine (ACT)) (Zhu CQ, Ding K., Strumpf D, Weir B A et al. Prognostic and predictive gene signature for adjuvant chemotherapy in resected non-small-cell lung cancer. J Clin Onco/2010 Oct. 10; 28(29):4417-24. PMID: 20823422). Gene expression data were quantified by using whole genome DNA microarrays (HG-U133 plus 2.0, Affymetrix).

Figure 13:
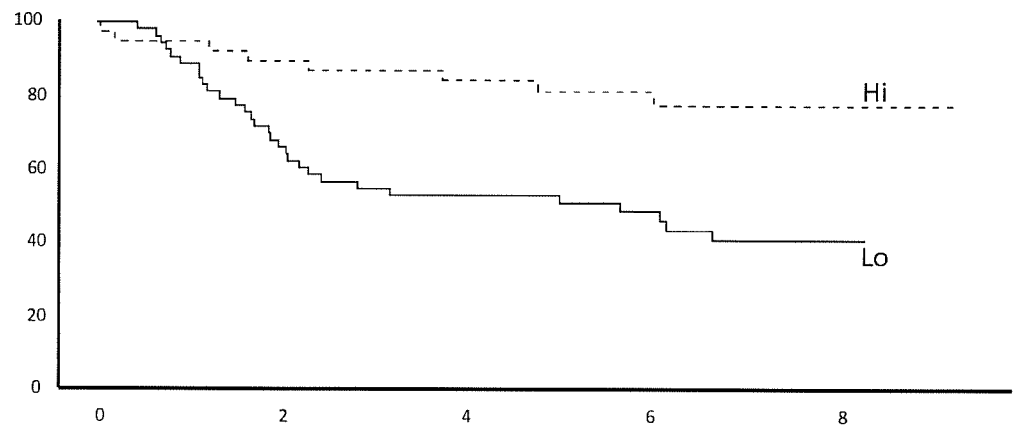

FIG. 13 shows the survival time (DFS in months) of a patients having a lung cancer separated in 2 groups: "low levels" (Lo) for patient having a score of I0-I8 and "high levels" (Hi) for patients having a score of I9-I17 determined with 17 genes (CCR2, CD3D, CD3E, CD3G, CD8A, CXCL11, GZMA, GZMB, GZMK, GZMM, IL15, IRF1, PRF1, STAT1, CD69, STAT4, and CCL2). Gene expression profiling was conducted on mRNA isolated from 90 frozen JBR.10 tumor samples (either from patients under observation [OBS], or treated with adjuvant cisplatin/vinorelbine (ACT)) (Zhu C Q, Ding K., Strumpf D, Weir B A et al. Prognostic and predictive gene signature for adjuvant chemotherapy in resected non-small-cell lung cancer. J Clin Onco/2010 Oct. 10; 28(29):4417-24. PMID: 20823422). Gene expression data were quantified by using whole genome DNA microarrays (HG-U133 plus 2.0, Affymctrix).

Figure 14:
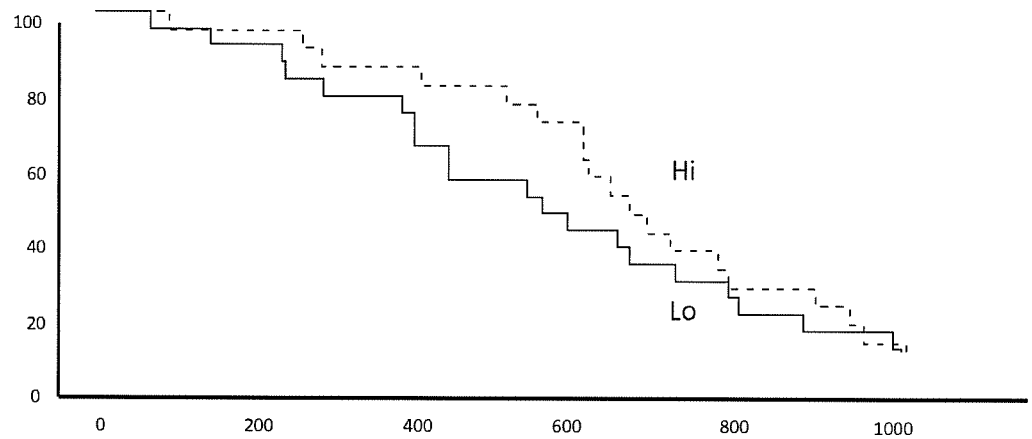

FIG. 14 shows the survival time (DFS in months) in a cohort of 44 patients having a melanoma separated in 2 groups: "low levels" (Lo) for patient having a score of I0-I10 and "high levels" (Hi) for patients having a score of I11-I21 determined with 21 genes. The data were established from the cohort described in Bogunovic D, ONeill D W, Belitskaya-Levy I, Vacic vet al. lmmune profile and mitotic index of metastatic melanoma lesions enhance eli ni cal staging in predicting patient survival. P roc Nat/Acad Sci USA 2009 Dec. 1; 106(48):20429-34. PMID: 19915147.

Figure 15:
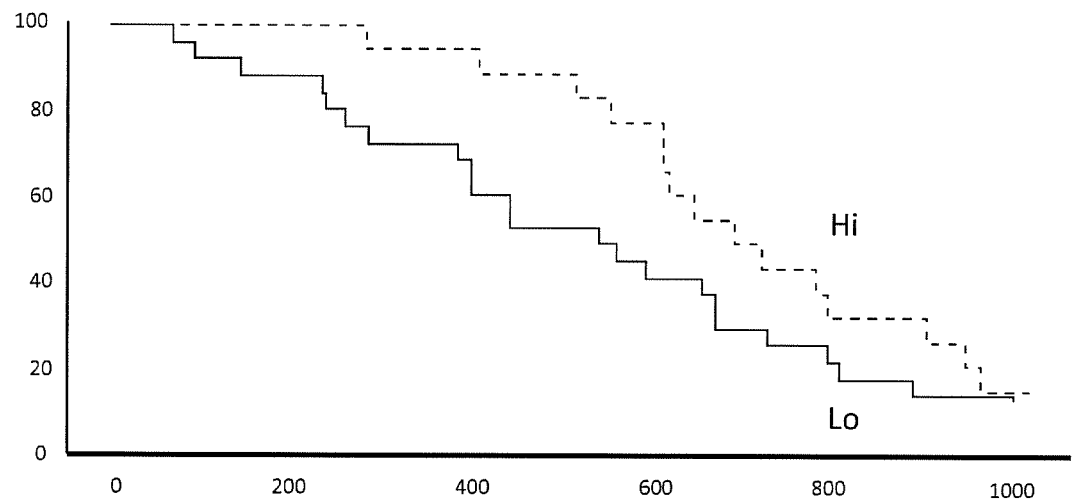

FIG. 15 shows the survival time (DFS in months) in a cohort of 44 patients having a melanoma separated in 2 groups: "low levels" (Lo) for patient having a score of I0-I8 and "high levels" (Hi) for patients having a score of I9-I16 determined with 16 genes (CCR2, CD3D, CD3E, CD3G, CD8A, CXCL10, GZMA, GZMB, GZMK, GZMM, IRF1, PRF1, CD69, ICOS, CXCR3 and TBX21). The data were established from the cohort described in Bogunovic D, ONeill D W, Belitskaya-Levy I, Vacic vet al. lmmune profile and mitotic index of metastatic melanoma lesions enhance eli ni cal staging in predicting patient survival. P roc Nat/Acad Sci USA 2009 Dec. 1; 106(48):20429-34. PMID: 19915147.

Figure 16:
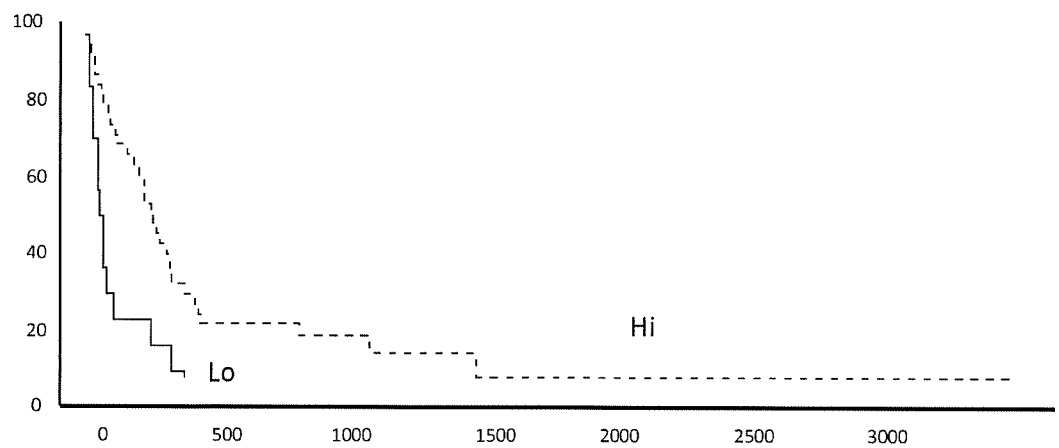

FIG. 16 shows the survival time (DFS in months) in a cohort of 57 patients having a melanoma (stage IV melanomas) separated in 2 groups: "low levels" (Lo) for patient having a score of I0-I10 and "high levels" (Hi) for patients having a score of I11-I21 determined with 21 genes. The global gene expression data come from 57 patients (Jonsson G, Busch c, Knappskog s, Geisler Jet al. Gene expression profiling-based identification of molecular subtypes in stage IV melanomas with different clinical outcome. Clin cancer Res 2010 Jul.1; 16(13):3356-67. PMID: 20460471.)

Figure 17:
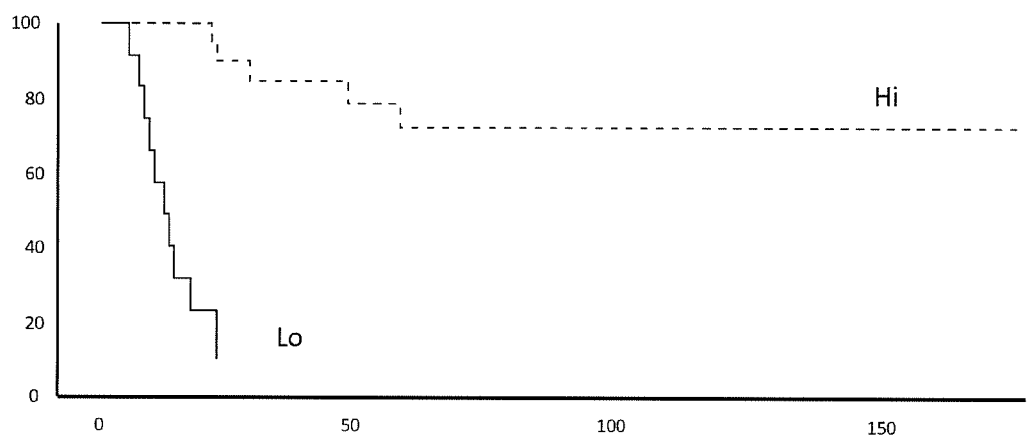

FIG. 17 shows the survival time (DFS in months) of patients having an ovarian cancer separated in 2 groups: "low levels" (Lo) for patient having a score of I0-I8 and "high levels" (Hi) for patients having a score of I9-I17 determined with 17 genes (CD3D, CD3E, CD3G, CD8A, CXCL10, CXCL11, GZMA, GZMB, GZMK, IRF1, PRF1, STAT1, ICOS, CXCR3, STAT4, CCL2, and TBX21). The cohort comprises sixteen early and sixteen advanced stage ovarian carcinomas, matched for histological subtype and differentiation grade (Zaal A, Peyrot W J, Berns P M, van der Burg M E, Veerbeek J H, Trimbos J B, Cadron I, van Diest P J, van Wieringen W N, Krijgsman O, Meijer G A, Pick J M, Timmers P J, Vergote I, Verheijen R H, Ylstra B, Zweemer R P; EORTC GCG Translational Research Group. Genomic aberrations relate early and advanced stage ovarian cancer. Cell Oncol (Dordr). 2012 June; 35(3):181-8. doi: 10.1007/s13402-012-0077-5. Epub 2012 May 12).

Figure 18:
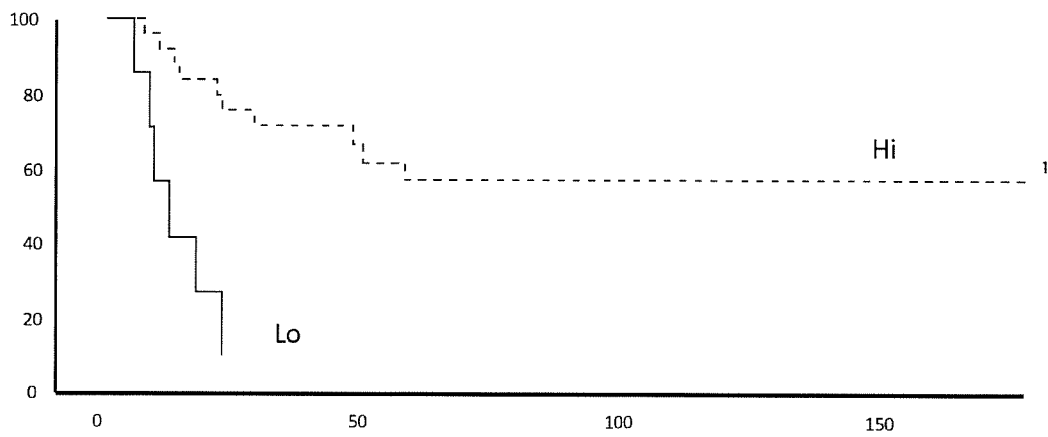

FIG. 18 shows the survival time (DFS in months) of patients having an ovarian cancer separated in 2 groups: "low levels" (Lo) for patient having a score of I0-I6 and "high levels" (Hi) for patients having a score of I7-I13 determined with 13 genes (CD3E, CD3G, CXCL10, CXCL11, GZMB, GZMK, IRF1 PRF1, STAT1, ICOS, CXCR3, CCL2, and TBX21). The cohort comprises sixteen early and sixteen advanced stage ovarian carcinomas, matched for histological subtype and differentiation grade (Zaal A, Peyrot W J, Berns P M, van der Burg M E, Veerbeek J H, Trimbos J B, Cadron I, van Diest P J, van Wieringen W N, Krijgsman O, Meijer G A, Piek J M, Timmers P J, Vergote I, Verheijen R H, Ylstra B, Zweemer R P; EORTC GCG Translational Research Group. Genomic aberrations relate early and advanced stage ovarian cancer. Cell Oncol (Dordr). 2012 June; 35(3):181-8. doi: 10.1007/s13402-012-0077-5. Epub 2012 May 12).

Figure 19:
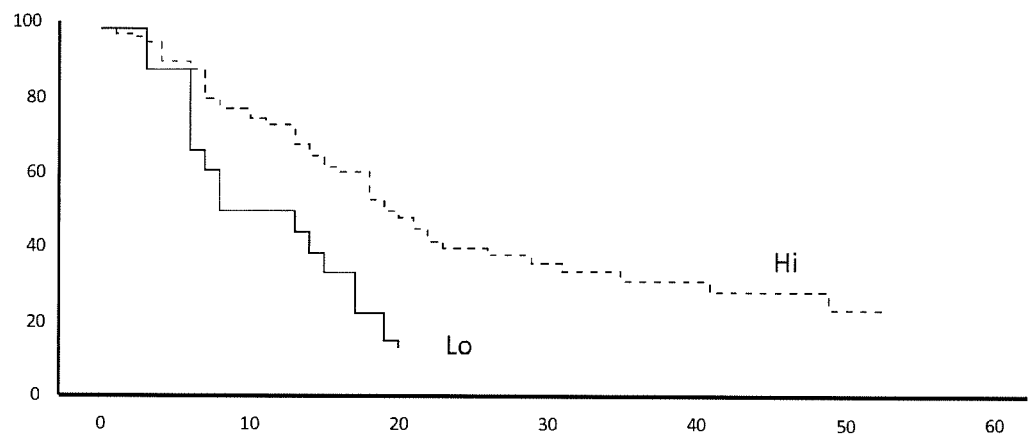

FIG. 19 shows the survival time (DFS in months) of patients having a pancreatic cancer separated in 2 groups: "low levels" (Lo) for patient having a score of I0-I7 and "high levels" (Hi) for patients having a score of I8-I14 determined with 14 genes (CD3G, CD8A, CXCL11, GZMA, GZMK, GZMM, IL15, IRF1, PRF1, STAT1, ICOS, CXCR3, STAT4, and TBX21). The cohort comprises 15 patients with resected primary PDAC from the University of North Carolina at Chapel Hill (UNC) and 15 patients with metastatic PDAC from the University of Nebraska Medical Center Rapid Autopsy Pancreatic Program (NEB) (Stratford J K, Bentrem D J, Anderson J M, Fan c et al. A six-gene signature predicts survival of patients with localized pancreatic ductal adenocarcinoma. PLoS Med 2010 Jul. 13; 7(7) :e1000307. PMID: 20644708).

Figure 20:
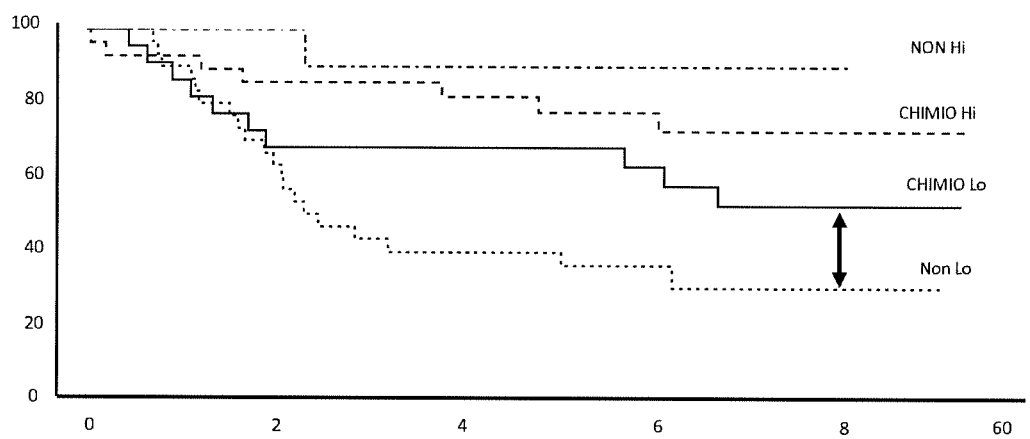

FIG. 20 shows the survival time of patients (Overall Survival (OS)) with a non metastatic lung cancer separated in 2 groups: "low levels" (Lo) for patient having a score of I0-I10 and "high levels" (Hi) for patients having a score of I11-I21. The patients received a chemotherapeutic treatment ("CHIMIO") or did not receive a chemotherapeutic treatment ("NON").

Figure 21:
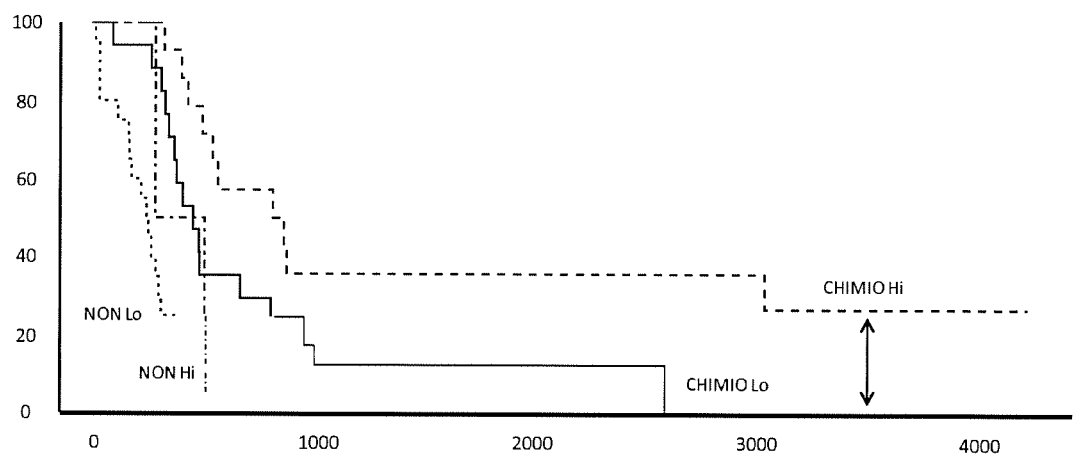

FIG. 21 shows the survival time of patients with a metastatic ovarian cancer (stage III/IV) separated in 2 groups: "low levels" (Lo) for patient having a score of I0-I10 and "high levels" (Hi) for patients having a score of I11-I21. The patients received a chemotherapeutic treatment ("CHIMIO") or did not receive a chemotherapeutic treatment ("NON").

EXAMPLE 1

Material & Methods

Patients and Database:

The records of colorectal cancer (CRC) patients who underwent a primary resection of their tumor at the Laennec-HEGP Hospitals between 1996 and 2004 were reviewed and previously described (Galon et al. 2006). Frozen tumor samples available from Laennec-HEGP Hospitals from 1996-2004, with sufficient RNA quality and quantity, were selected (validation cohort 1, n=108). The RNA samples analyzed were from 108 different patients. These patients were used for gene expression experiments (Taqman cohort). The observation time in the cohorts was the interval between diagnosis and last contact (death or last follow-up). Data were censored at the last follow-up for patients without relapse, or death. The min:max values until progression/ death or last follow-up were (0:136) months, respectively. Three patients for whom follow-up data were unavailable were excluded from survival analysis. Time to recurrence or disease-free time was defined as the interval from the date of surgery to confirmed tumor relapse date for relapsed patients and from the date of surgery to the date of last follow-up for disease-free patients.

Histopathological and clinical findings were scored according to the UICC-TNM staging system. Post-surgical patient surveillance was performed at Laennec-HEGP Hospitals for all patients according to general practice for CRC patients. Adjuvant chemotherapy was administered or not to patients with stage II and III CRCs, and palliative chemotherapy to patients with advanced colorectal cancers (stage IV) and to patients without complete resection of the tumor. Adjuvant chemotherapy was fluorouracil (FU)-based. Follow-up data were collected prospectively and updated. A secure Web-based database, TME.db (Tumor MicroEnvironment Database), was built on a 3-tier architecture using Java-2 Enterprise-Edition (J2EE) to integrate the clinical data and the data from high-throughput technologies.

Gene Expression Analysis:

Tissue samples were snap-frozen within 15 minutes after surgery and stored in liquid nitrogen. Frozen tumor samples (cohort 1, n=108) of randomly selected patients available from Laennec-HEGP Hospitals (1996-2004), with sufficient RNA quality and quantity, were selected for gene expression analysis. The RNA samples analyzed were from 108 different patients. Total RNA was isolated by homogenization with RNeasy isolation-kit (Qiagen, Valencia, CA). The integrity and the quantity of the RNA were evaluated on a bioanalyzer-2100 (Agilent Technologies, Palo Alto, CA). RT-PCR experiments were performed according to the manufacturer's instructions (Applied-Biosystems, Foster City, CA). Quantitative real-time TaqMan-PCR was performed using Low-Density-Arrays and the 7900 robotic real-time PCR-system (Applied-Biosystems). 18S ribosomal RNA primers and probe were used as internal control. Gene expression analyses were performed using Ct-values (threshold cycle) normalized to 18S ribosomal RNA (ΔCt). Data were analyzed using the SDS Software v2.2 (Applied-Biosystems) and TME statistical module.

Results

Figure 1:
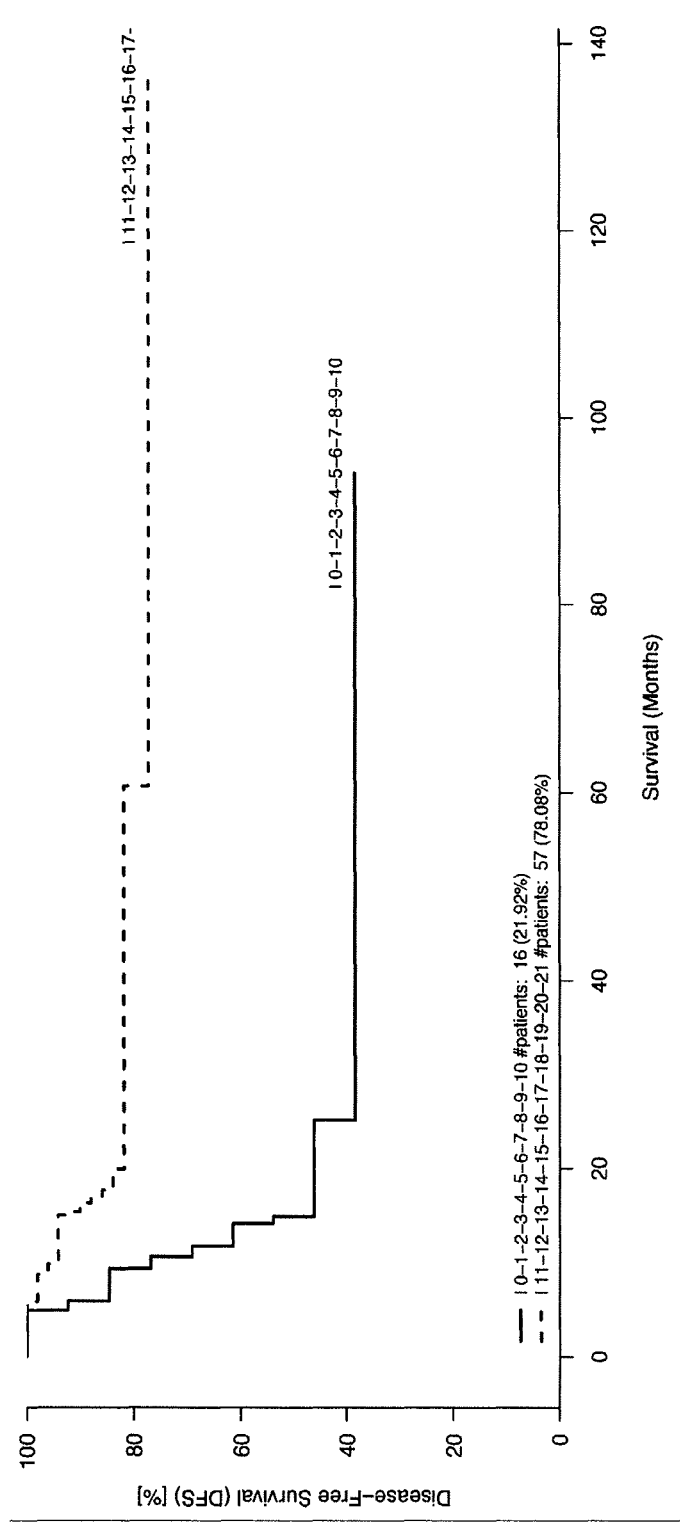
FIG. 1 shows the survival time of patients with a non metastatic colorectal cancer separated in 2 groups: "low levels" for patient having a score of I0-I10 and "high levels" for patients having a score of I11-I21.
Figure 2:
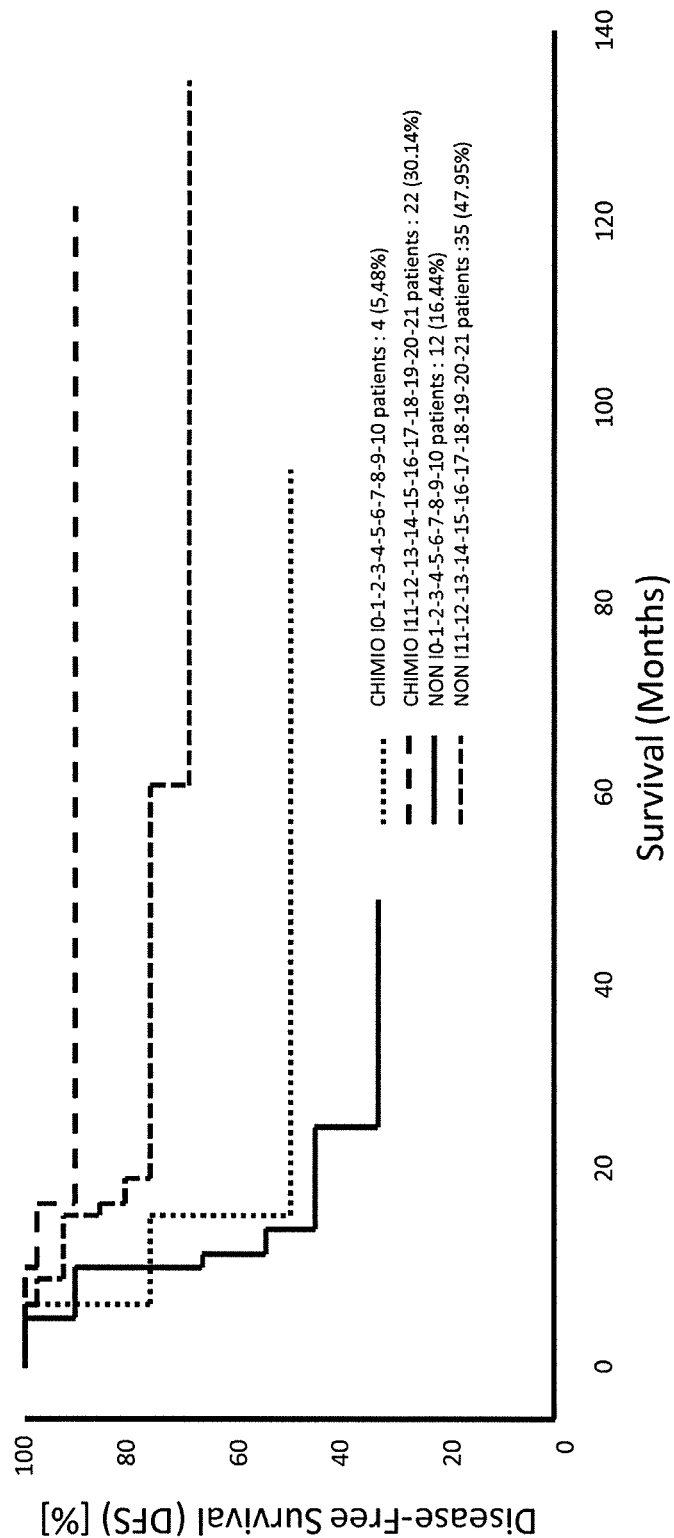
FIG. 2 shows the survival time of patients with a non metastatic colorectal cancer separated in 2 groups: "low levels" for patient having a score of I0-I10 and "high levels" for patients having a score of I11-I21. The patients received a chemotherapeutic treatment ("CHIMIO") or did not receive a chemotherapeutic treatment ("NON").
Figure 3:
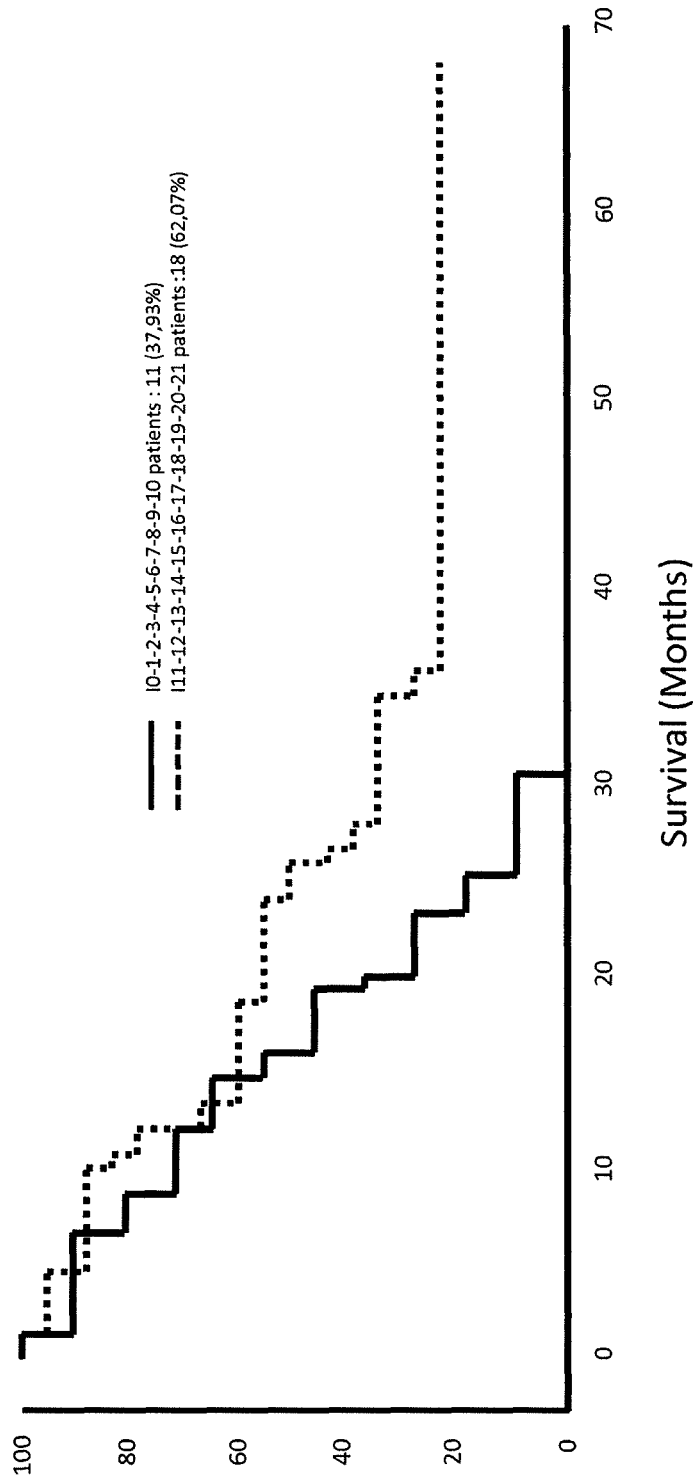
FIG. 3 shows the survival time of patients (Overall Survival (OS)) with a metastatic colorectal cancer separated in 2 groups: "low levels" for patient having a score of I0-I10 and "high levels" for patients having a score of I11-I21.
Figure 4:
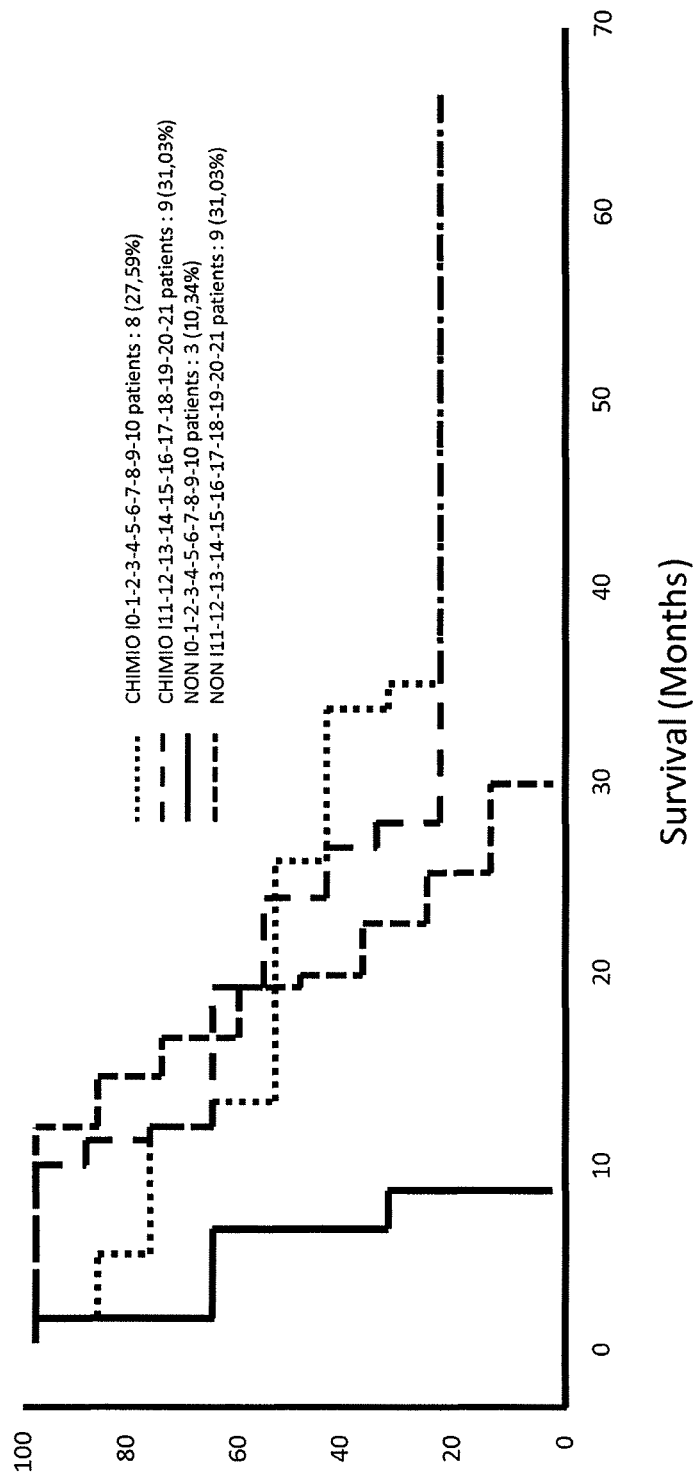
FIG. 4 shows the survival time of patients (Overall Survival (OS)) with a metastatic colorectal cancer separated in 2 groups: "low levels" for patient having a score of I0-I10 and "high levels" for patients having a score of I11-I21. The patients received a chemotherapeutic treatment ("CHIMIO") or did not receive a chemotherapeutic treatment ("NON").
Figure 5:
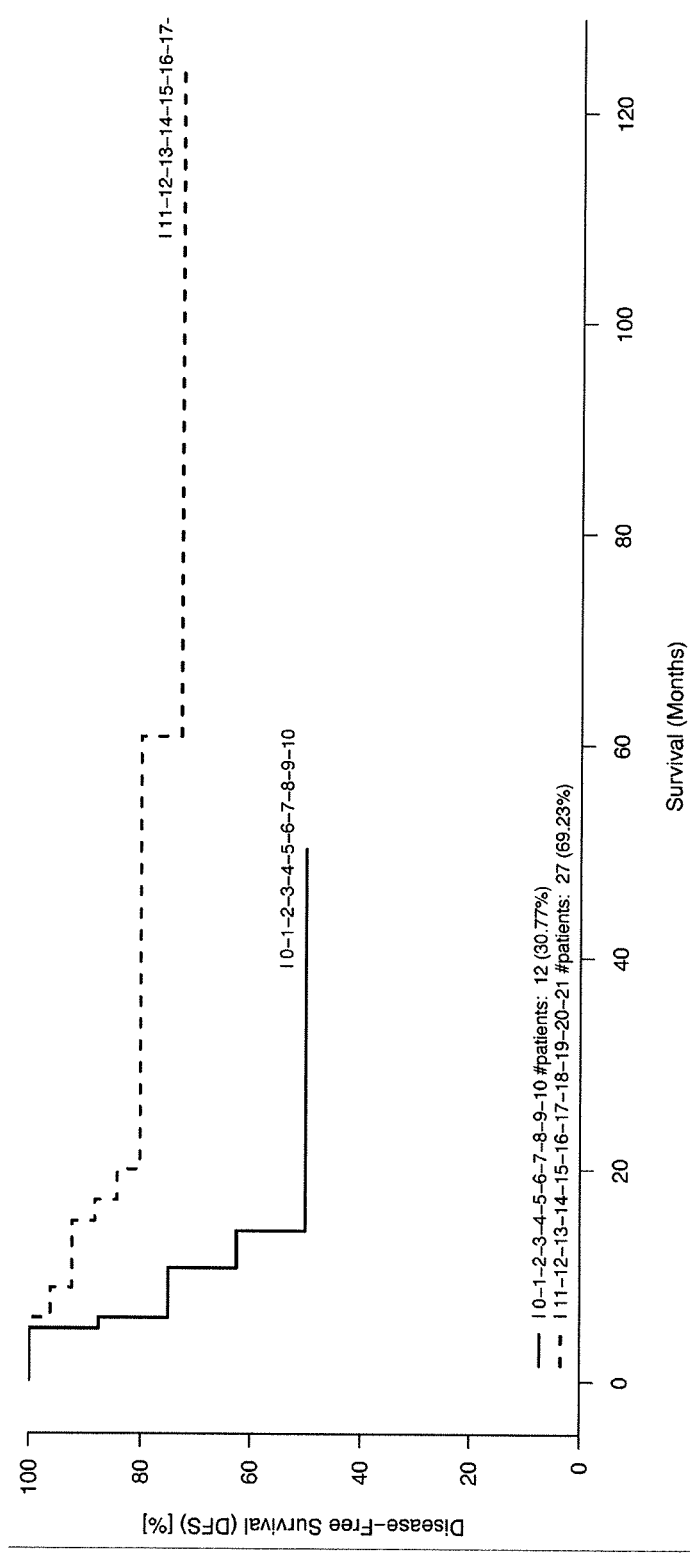
FIG. 5 shows the survival time of patients with an early advanced non metastatic colorectal cancer (Stage II TNM) separated in 2 groups: "low levels" for patient having a score of I0-I10 and "high levels" for patients having a score of I11-I21.
Figure 6:
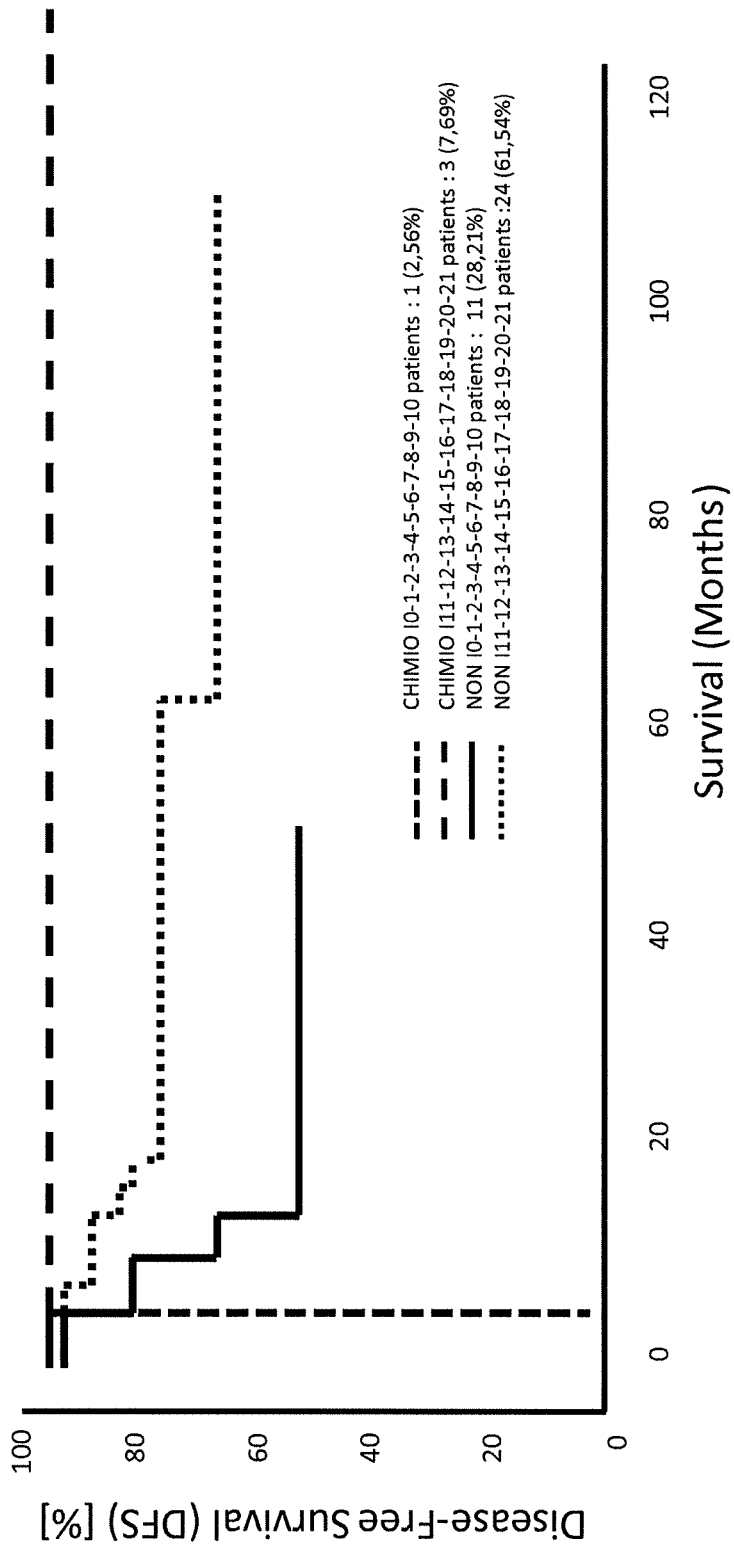
FIG. 6 shows the survival time of patients with an early advanced non metastatic colorectal cancer (Stage II TNM) separated in 2 groups: "low levels" for patient having a score of I0-I10 and "high levels" for patients having a score of I11-I21. The patients received a chemotherapeutic treatment ("CHIMIO") or did not receive a chemotherapeutic treatment ("NON").

We determined the expression levels (EL) of genes CCR2, CD3D, CD3E, CD3G, CD8A, CXCL10, CXCL11, GZMA, GZMB, GZMK, GZMM, IL15, IRF1, PRF1, STAT1, CD69, ICOS, CXCR3, STAT4, CCL2, and TBX2 in the tumor samples. The predetermined reference values (ELR) were previously determined according to WO2007045996 and Jerome Galon, et al. (Type, Density, and Location of Immune Cells Within Human Colorectal Tumors Predict Clinical Outcome Science 313, 1960 (2006); DOI: 10.1126/science.1129139). We then built a score as follows: I0 when 0 gene has its expression level higher than its predetermined reference value (i.e. all genes have their expression levels lower than their predetermined reference levels) and In (I1-I21)when n genes has their expression level higher than their respective predetermined reference value. For the sake of clarity in the interpretation of the results we separate the patients in 2 groups : "low levels" for patient having a score of I0-I10 and "high levels" for patients having a score of I11-I21 KM curves were then drawn for the 2 groups of patients. The results are depicted in FIGS. 1-6. We determined that higher the score is, longer the survival time of the patients will be, whatever is the stage of the patient (non metastatic or metastatic patients) (FIGS. 1, 3 and 4). Interestingly, for non metastatic colorectal cancer we determined that patients having a high score advantageously benefited from a chemotherapeutic treatment in comparison with patients having a low score (FIG. 2). On the contrary, for metastatic colorectal cancer we determined that patients having a low score advantageously benefited from a chemotherapeutic treatment in comparison with patients having a low score (FIG. 4). More interestingly, for early advanced non metastatic colorectal cancer (stage II) we determined that patients having a high score advantageously benefited from a chemotherapeutic treatment in comparison with patients having a low score (FIG. 6). Accordingly, for said category of patients for which there exist no current guideline for selecting patients eligible for a chemotherapeutic patient, the identified signature would be very helpful for determining whether a patient would advantageously receive a chemotherapeutic treatment.

EXAMPLE 2

The signature of 21 genes identified in EXAMPLE 1 was validated for predicting the survival time of patients suffering of breast cancer, cervical cancer, hepatocellular carcinoma, lung cancer, melanoma, ovarian cancer or pancreatic cancer (see for example FIGS. 7, 12, 14 and 16). Minimal signatures of at least 7 genes also were determined (see FIGS. 8, 9, 10, 11, 13, 15, 17, 18 and 19).

EXAMPLE 3

FIG. 20 illustrates stage IB-IIV lung cancer patients (NSCLC), where patient with a "Hi" adaptive immune gene signature have prolonged survival and do not need chemotherapy treatment (no benefit from chemotherapy treatment). A significant benefic effect of chemotherapy treatment can be observed in patients with a "Lo" adaptive immune gene signature.

FIG. 21 illustrates stage III/IV ovarian cancer patients, where patient with a "Hi" adaptive immune gene signature have a significant benefic effect of chemotherapy treatment.

On the contrary patients with a "Lo" adaptive immune gene signature prolonged survival and do not need chemotherapy treatment (no benefit from chemotherapy treatment).

REFERENCES

Throughout this application, various references describe the state of the art to which this invention pertains. The disclosures of these references are hereby incorporated by reference into the present disclosure.

The invention claimed is:

1. A method for treating a patient suffering from a lymphoma, wherein said method comprises the steps of: i) measuring in a tumor sample obtained from the patient, prior to anti-cancer treatment, the gene expression level of at least all of the following genes: CCR2, CD3D, CD3E, CD3G, CD8A, CXCL10, CXCL11, GZMA, GZMB, GZMK, GZMM, IL15, IRF1, PRF1, STAT1, CD69, ICOS, CXCR3, STAT4, CCL2, and TBX21; ii) comparing every expression level determined at step i) with a corresponding predetermined reference value; iii) selecting the patient as being a responder to at least one immunotherapy when all expression levels determined at step i) are either higher or lower than the corresponding predetermined reference value; and iv) administering said immunotherapy to said patient assessed as being a responder thereto in step iii), wherein said at least one immunotherapy is an antibody directed against any one of CTLA4, PD1, PDL1, TIM3, LAG3, B7H3, B7H4, TREM, BTLA, LIGHT or B7H6; or an immune cell selected from T cells, NK cells, dendritic cells or B cells; or any combination thereof.

2. The method according to claim 1, wherein the lymphoma is Hodgkin's disease or a non-Hodgkin's lymphoma.

* * * * *